United States Patent
Kheradvar

(10) Patent No.: US 10,629,096 B2
(45) Date of Patent: Apr. 21, 2020

(54) CALCIFIED POLYMERIC VALVE AND VESSELS FOR VALVE-IN-VALVE APPLICATIONS

(71) Applicant: THE REGENTS OF THE UNIVERSITY OF CALIFORNIA, Oakland, CA (US)

(72) Inventor: Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/265,593

(22) Filed: Sep. 14, 2016

(65) Prior Publication Data

US 2017/0076637 A1    Mar. 16, 2017

Related U.S. Application Data

(60) Provisional application No. 62/218,221, filed on Sep. 14, 2015.

(51) Int. Cl.
*A61F 2/24* (2006.01)
*G09B 23/32* (2006.01)
*G09B 23/30* (2006.01)

(52) U.S. Cl.
CPC ............ *G09B 23/32* (2013.01); *A61F 2/2412* (2013.01); *A61F 2/2463* (2013.01); *G09B 23/30* (2013.01); *A61F 2/24* (2013.01)

(58) Field of Classification Search
CPC ..... A61F 2/2463; A61F 2/2412; G09B 23/30; G09B 23/32; G09B 23/303; B33Y 80/00; B29C 64/00
See application file for complete search history.

(56) References Cited

U.S. PATENT DOCUMENTS

| 7,785,615 B2 * | 8/2010 | Dave | A61L 27/446 424/422 |
| 2007/0254273 A1 * | 11/2007 | Lafrance | A61F 2/2472 434/272 |
| 2016/0303804 A1 * | 10/2016 | Grbic | G09B 23/285 |

OTHER PUBLICATIONS

STIC Search Results.*
Zadeh et al.; In-vitro calcification study of polyurethane heart valves; Materials Science and Engineering; C35 (2014);p. 335-340.*

(Continued)

*Primary Examiner* — Dinah Baria
(74) *Attorney, Agent, or Firm* — Tope-McKay & Associates

(57) ABSTRACT

Described is a group of polymeric calcific heart valves with different levels of calcification that can be used for research and development studies related to transcatheter heart valve technologies. Using a heart flow simulator, the valves' function was studied in aortic position in the presence or absence of an implanted transcatheter aortic valve (valve-in-valve). Through multiple experiments based on echocardiography, it was found that these calcific valves can suitably mimic the function of a native calcified stenotic aortic valve and can be used for valve-in-valve studies. Using this novel polymeric calcified valve provides a desired cost-saving solution for testing the performance of new TAVR systems in vitro and in vivo.

10 Claims, 22 Drawing Sheets
(17 of 22 Drawing Sheet(s) Filed in Color)

(56) References Cited

OTHER PUBLICATIONS

Simon et al.; In vivio bone response to 3D periodic hydroxyapatite scaffolds assembled by direct ink writing; Journal of Biomedical Materials Research Oart A DOI 10.1002; 2007; pp. 747-758.*

Rayner J, Coffey S, Newton J, Prendergast BD. Aortic valve disease. International Journal of Clinical Practice. 2014, pp. 1209-1215.

Nkomo VT, Gardin JM, Skelton TN, Gottdiener JS, Scott CG, Enriquez-Sarano M. Burden of valvular heart diseases: A population-based study, Sep. 16, 2006, The Lancet.368: pp. 1005-1011.

Kheradvar A, Groves E, Goergen C, Alavi SH, Tranquillo R, Simmons C, Dasi L, Grande-Allen KJ, Mofrad MK, Falahatpisheh A, Griffith B, Baaijens F, Little S, Canic S. Emerging trends in heart valve engineering: Part ii. Novel and standard technologies for aortic valve replacement. Annals of Biomedical Engineering. 2015;43: pp. 844-857.

Miller JD, Weiss RM, Heistad DD. Calcific aortic valve stenosis: Methods, models, and mechanisms. Circulation Research. 2011;108: pp. 1392-1412.

Cheek JD, Wirrig EE, Alfieri CM, James JF, Yutzey KE. Differential activation of valvulogenic, chondrogenic, and osteogenic pathways in mouse models of myxomatous and calcific aortic valve disease. Journal of Molecular and Cellular Cardiology. 2012;52: pp. 689-700.

Zhang B, Casaclang-Verzosa, G., Miller, J.D. Mouse models of calcific aortic valve disease. In: Rajamannan NM, ed. Molecular biology of valvular heart disease. Springer; 2014: pp. 67-80.

Kheradvar A, Groves EL, Tseng EE. Proof of concept of foldavalve a novel 14fr totally repositionable and retrievable transcatheter aortic valve. Euro Intervention. 2015;10:pii: 20141002-20141001, pp. 1-7.

Emmert MY, Weber B, Behr L, Sammut S, Frauenfelder T, Wolint P, Scherman J, Bettex D, Grünenfelder J, Falk V, Hoerstrup SP. Transcatheter aortic valve implantation using anatomically oriented, marrow stromal cell-based, stented, tissue-engineered heart valves: Technical considerations and implications for translational cell-based heart valve concepts. European Journal of Cardio-Thoracic Surgery. 2014;45: pp. 61-68.

Wendt D, Pasa S, Kahlert P, Delaloye S, Al-Rashid F, Price V, Jánosi R-A, Borenstein N, Behr L, Konorza T, Erbel R, Jakob H, Thielmann M. A new self-expandable transcatheter aortic valve for transapical implantation: Feasibility in acute and chronic animal experiments. Scandinavian Cardiovascular Journal. 2013;47: pp. 145-153.

Emmert MY, Weber B, Wolint P, Behr L, Sammut S, Frauenfelder T, Frese L, Scherman J, Brokopp CE, Templin C, Grünenfelder J, Zünd G, Falk V, Hoerstrup SP. Stem cell-based transcatheter aortic valve implantation: First experiences in a pre-clinical model. JACC: Cardiovascular Interventions. 2012;5: pp. 874-883.

Kheradvar A, Gharib M. On mitral valve dynamics and its connection to early diastolic flow. Ann Biomed Eng. 2009;37: pp. 1-13.

Kheradvar A, Kasalko J, Johnson D, Gharib M. An in vitro study of changing profile heights in mitral bioprostheses and treir influence on flow. ASAIO J. 2006;52: pp. 34-38.

Falahatpisheh A, Kheradvar A. High-speed particle image velocimetry to assess cardiac fluid dynamics in vitro: From performance to validation. European Journal of Mechanics—B/Fluids. 2012;35: pp. 2-8.

Groves EM, Falahatpisheh A, Su JL, Kheradvar A. The effects of positioning of transcatheter aortic valves on fluid dynamics of the aortic root. ASAIO journal. 2014;60: pp. 545-552.

Baumgartner H, Hung J, Bermejo J, Chambers JB, Evangelista A, Griffin BP, Iung B, Otto CM, Pellikka PA, Quinones M. Echocardiographic assessment of valve stenosis: Eae/ase recommendations for clinical practice. J Am Soc Echocardiogr. 2009;22:1-23; pp. 101-102.

Nishimura RA, Otto CM, Bonow RO, Carabello BA, Erwin JP, 3rd, Guyton RA, O'Gara PT, Ruiz CE, Skubas NJ, Sorajja P, Sundt TM, 3rd, Thomas JD. 2014 aha/acc guideline for the management of patients with valvular heart disease: A report of the american college of cardiology/american heart association task force on practice guidelines. J Am Coll Cardiol. 2014;63: pp. e57-e185.

Cribier A, Eltchaninoff H, Bash A, Borenstein N, Tron C, Bauer F, Derumeaux G, Anselme F, Laborde F, Leon MB. Percutaneous transcatheter implantation of an aortic valve prosthesis for calcific aortic stenosis: First human case description. Circulation. 2002;106: pp. 3006-3008.

Faxon DP. Transcatheter aortic valve implantation: Coming of age. Circulation. 2011;124: pp. e439-e440.

Webb J, Cribier A. Percutaneous transarterial aortic valve implantation: What do we know? Eur Heart J. 2011;32: pp. 140-147.

Smith CR, Leon MB, Mack MJ, Miller DC, Moses JW, Svensson LG, Tuzcu EM, Webb JG, Fontana GP, Makkar RR, Williams M, Dewey T, Kapadia S, Babaliaros V, Thourani VH, Corso P, Pichard AD, Bavaria JE, Herrmann HC, Akin JJ, Anderson WN, Wang D, Pocock SJ. Transcatheter versus surgical aortic-valve replacement in high-risk patients. N Engl J Med. 2011;364: pp. 2187-2198.

Leon MB, Smith CR, Mack M, Miller DC, Moses JW, Svensson LG, Tuzcu EM, Webb JG, Fontana GP, Makkar RR, Brown DL, Block PC, Guyton RA, Pichard AD, Bavaria JE, Herrmann HC, Douglas PS, Petersen JL, Akin JJ, Anderson WN, Wang D, Pocock S. Transcatheter aortic-valve implantation for aortic stenosis in patients who cannot undergo surgery. N Engl J Med. 2010;363: pp. 1597-1607.

Kutting M, Roggenkamp J, Urban U, Schmitz-Rode T, Steinseifer U. Polyurethane heart valves: Past, present and future. Expert Rev Med Devices. 2011;8: pp. 227-233.

Ladich E, Nakano M, Virmani R. Pathologic findings in aortic stenosis. In: Min JK, ed. Multimodality imaging for transcatheter aortic valve replacement. London, UK: Springer; 2014: pp. 145-156.

* cited by examiner

CALCIFIED POLYMERIC VALVE AND VESSELS FOR VALVE-IN-VALVE APPLICATIONS

CROSS-REFERENCE TO RELATED APPLICATIONS

This is a non-provisional application of U.S. Provisional Application No. 62/218,221, filed on Sep. 14, 2015.

BACKGROUND OF THE INVENTION (1) Field of Invention

The present invention relates to heart valves and vessels and, more particularly, to calcified polymeric valves and vessels having calcium appetite inclusions immersed therein.

(2) Description of Related Art

Valvular heart disease is the third-most common cause of heart problems in the United States. Aortic valve stenosis significantly affects a patient's quality of life once it is advanced (see the List of Incorporated Literature References, Literature Reference No. 1), and affects between two to percent of the elderly population, according to epidemiological studies (see Literature Reference No. 2). Calcification is by far the major cause of aortic valve stenosis (more than 80%), and among the affected patients, some have certain types of triggering congenital heart defects such as bicuspid valve or a history of rheumatic heart disease (see Literature Reference No. 1). Calcific aortic valve stenosis is a progressive disease, which is irreversible and can be fatal if left untreated. Pharmacological agents cannot currently prevent valvular calcification or help repair a damaged valve, since valve tissue is unable to spontaneously regenerate. Thus, aortic valve replacement/repair is the only current available treatment.

The introduction of transcatheter aortic valve replacement (TAVR) has revolutionized heart valve replacement procedures by offering minimally invasive treatment options for high-risk patients who have been considered unfit for traditional open-heart surgery. TAVR involves delivery, deployment, and implantation of a crimped, stented valve within the aortic annulus. A narrow range of FDA-approved transcatheter valves is currently being used in elderly patients with calcific aortic stenosis (see Literature Reference No. 3). Transcatheter aortic valves share similarities with bioprosthetic surgical heart valves, as both possess tissue leaflets. However, their major difference is the housing of the valves' leaflets within a stent. Contrary to the surgically-implantable aortic valves, transcatheter valves are not sewn within the aortic annulus but their stent expands within the native calcific aortic valve and the roughness due to the calcific nodules on the native leaflets provides means to hold the stented valve in place. The patterns of calcific nodules developed on the leaflets are completely random and vary in every patient.

Calcific aortic stenosis is mainly a disease of the human and has not ever been reported to naturally occur in animals. Very few attempts have been made to develop animal models with calcific aortic stenosis that were mainly mouse models (see Literature Reference Nos. 4-6), and no large animal model of calcific aortic stenosis is yet available. Lack of such an animal model makes the research and development studies related to prosthetic heart valves very difficult and costly. Most technologies related to transcatheter repair/replacement of aortic valve require a calcified heart valve in animals to show their feasibility. Currently, the preclinical studies related to TAVR have been performed on ovine or swine models with normal aortic valve (see Literature Reference Nos. 7-10). However, the experiments do not closely reflect the actual clinical situation, since these animals possess normal aortic valves without any trace of calcification. Therefore, not only a successful implant in sheep does not guarantee that the valve can similarly perform in a patient with calcific aortic valve but also a failed experiment due to lack of anchoring in the animal does not necessarily imply that the tested valve will fail in human with calcific aortic stenosis. Furthermore, since the calcific patterns in human aortic valve is remarkably heterogeneous, design and development of the TAVR systems suitable for most patients is extremely difficult due to the lack of a proper experimental model.

Thus, a continuing need exists for a valve whose leaflets possess calcium hydroxyapatite inclusions immersed in them and for valves that can be produced to replicate different grades of calcification (e.g., mild, moderate or severe) to test transcatheter aortic valve implantation in vitro or even in vivo. Such a calcified valve or vessel can be implanted in an experimental animal to have it prepared for a secondary device to be implanted therein to replicate a situation in a human that is considered a calsified or stenotic valve or vessel.

SUMMARY OF INVENTION

The present invention relates to heart valves and, more particularly, to a calcific polymeric valve for valve-in-valve applications. The calcific polymeric valve comprises a valve structure with at least two leaflets made of a polymeric material with calcium appetite inclusions immersed in it. In various embodiments, the calcium appetite is deliberately distributed within the valve elements or, in other aspects, is randomly distributed within the valve elements.

In another aspect, the calcium appetite has been carefully distributed within its elements to replicate a particular disease/patient situation.

In yet another aspect, the valve is implantable via transcatheter means or implantable surgically.

In yet another aspect, the valve is a heart valve or a venous valve.

In another aspect, the polymeric material is a silicone polymer or polyurethane.

Additionally, the valve is made according to radiologic images of patients as obtained from magnetic resonance imagining (MRI) or a computerized tomography (CT) scan.

In another aspect, the valve is formed by a three-dimensional (3D) printer.

In yet another aspect, this disclosure provides a vascular segment, comprising a vascular wall made of a polymeric material with calcium appetite inclusions immersed in the vascular wall.

In another aspect, the calcium appetite is deliberately distributed within the vascular wall, or the calcium appetite is randomly distributed within the vascular wall.

In another aspect, the vascular segment is implantable via transcatheter means.

In yet another aspect, the vascular segment is implantable surgically.

Further, the polymeric material in the vascular segment is a silicone polymer or polyurethane.

In another aspect, the vascular wall is made according to radiologic images of patients as obtained from magnetic resonance imagining (MRI) or a computerized tomography (CT) scan.

Further, the vascular wall is formed by a three-dimensional (3D) printer.

In another aspect, this disclosure provides a method for forming a calcific polymeric valve, comprising acts of making a mold to mimic a natural aortic valve; adding polyurethane into the mold to produce the leaflets of the valve; and adding a mixture of calcium phosphate and polyurethane to the mold, resulting in calcium appetite inclusions on the leaflets to replicate calcified nodules and deposits on the valve leaflets.

In yet another aspect, this disclosure provides a method for testing a deployable heart valve or stent, comprising acts of depositing a calcified polymeric valve or vessel in a living animal or laboratory equipment; implanting a secondary device within the calcified polymeric valve or vessel; and measuring operating characteristics of the secondary device. The secondary device is, for example, a deployable heart valve or a stent or stented valve.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The objects, features and advantages of the present invention will be apparent from the following detailed descriptions of the various aspects of the invention in conjunction with reference to the following drawings, where.

DETAILED DESCRIPTION

Figure 1:
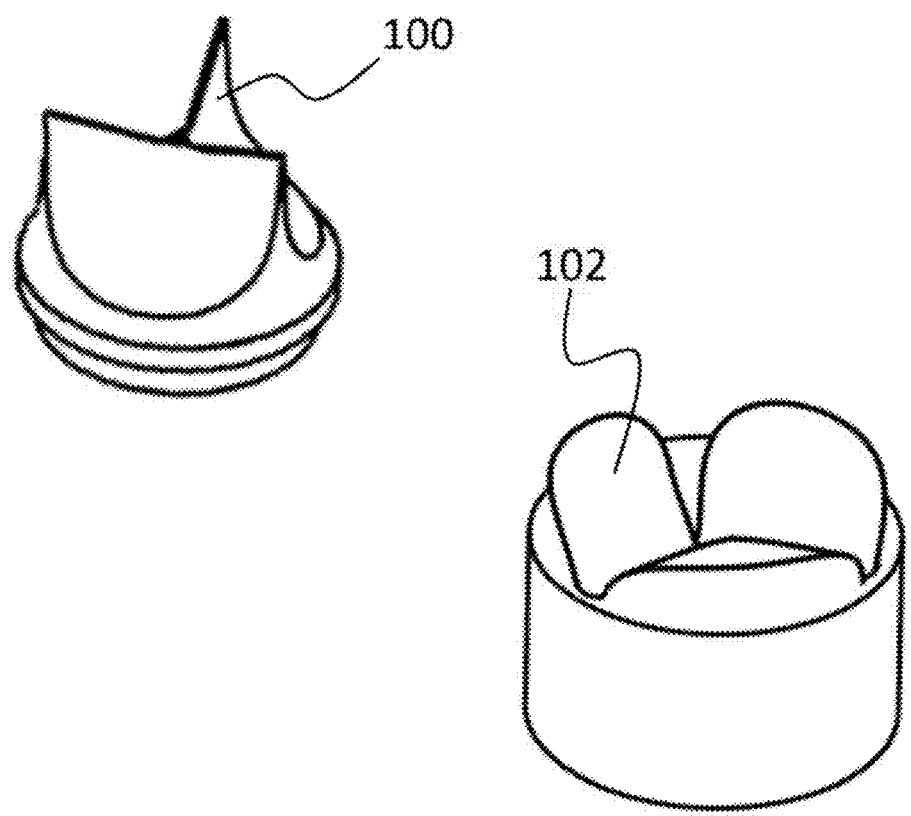
FIG. 1 is an illustration depicting a male and female piece of a heart valve according to various embodiments of the present invention.

The present invention relates to heart valves and, more particularly, to a calcific polymeric valve for valve-in-valve applications. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

Before describing the invention in detail, first a list of cited references is provided. Next, specific details of various embodiment of the present invention are provided to give an understanding of the specific aspects. Thereafter, experimental results are provided, followed by a follow-up discussion and a conclusion.

(1) LIST OF INCORPORATED LITERATURE REFERENCES

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Rayner J, Coffey S, Newton H, Prendergast B D. Aortic valve disease. *International Journal of Clinical Practice.* 2014:n/a-n/a
2. Nkomo V T, Gardin J M, Skelton T N, Gottdiener J S, Scott C G, Enriquez-Sarano M. Burden of valvular heart diseases: A population-based study. *The Lancet.* 368: 1005-1011
3. Kheradvar A, Groves E, Goergen C, Alavi S H, Tranquillo R, Simmons C, Dasi L, Grande-Allen K J, Mofrad M K, Falahatpisheh A, Griffith B, Baaijens F, Little S, Canic S. Emerging trends in heart valve engineering: Part ii. Novel and standard technologies for aortic valve replacement. *Annals of Biomedical Engineering.* 2015; 43:844-857
4. Miller J D, Weiss R M, Heistad D D. Calcific aortic valve stenosis: Methods, models, and mechanisms. *Circulation Research.* 2011; 108:1392-1412
5. Cheek J D, Wirrig E E, Alfieri C M, James J F, Yutzey K E. Differential activation of valvulogenic, chondrogenic, and osteogenic pathways in mouse models of myxomatous and calcific aortic valve disease. *Journal of Molecular and Cellular Cardiology.* 2012; 52:689-700
6. Zhang B, Casaclang-Verzosa, G., Miller, J. D. Mouse models of calcific aortic valve disease. In: Rajamannan N M, ed. *Molecular biology of valvular heart disease.* Springer; 2014:67-80.
7. Kheradvar A, Groves E L, Tseng E E. Proof of concept of foldavalve a novel 14fr totally repositionable and retrievable transcatheter aortic valve. *Euro Intervention.* 2015; 10:pii: 20141002-20141001.
8. Emmert M Y, Weber B, Behr L, Sammut S, Frauenfelder T, Wolint P, Scherman J, Bettex D, Grlnenfelder J, Falk V, Hoerstrup S P. Transcatheter aortic valve implantation using anatomically oriented, marrow stromal cell-based, stented, tissue-engineered heart valves: Technical considerations and implications for translational cell-based heart valve concepts. *European Journal of Cardio-Thoracic Surgery.* 2014; 45:61-68
9. Wendt D, Pasa S, Kahlert P, Delaloye S, Al-Rashid F, Price V, Janosi R-A, Borenstein N, Behr L, Konorza T, Erbel R, Jakob H, Thielmann M. A new self-expandable transcatheter aortic valve for transapical implantation: Feasibility in acute and chronic animal experiments. *Scandinavian Cardiovascular Journal.* 2013; 47:145-153
10. Emmert M Y, Weber B, Wolint P, Behr L, Sammut S, Frauenfelder T, Frese L, Scherman J, Brokopp C E, Templin C, Grünenfelder J, Zünd G, Falk V, Hoerstrup S P. Stem cell-based transcatheter aortic valve implantation: First experiences in a pre-clinical model. *JACC: Cardiovascular Interventions.* 2012; 5:874-883
11. Kheradvar A, Gharib M. On mitral valve dynamics and its connection to early diastolic flow. *Ann Biomed Eng.* 2009; 37:1-13
12. Kheradvar A, Kasalko J, Johnson D, Gharib M. An in vitro study of changing profile heights in mitral bioprostheses and their influence on flow. *ASAIO J.* 2006; 52:34-38
13. Falahatpisheh A, Kheradvar A. High-speed particle image velocimetry to assess cardiac fluid dynamics in vitro: From performance to validation. *European Journal of Mechanics—B/Fluids.* 2012; 35:2-8
14. Groves E M, Falahatpisheh A, Su J L, Kheradvar A. The effects of positioning of transcatheter aortic valves on fluid dynamics of the aortic root. *ASAIO journal.* 2014; 60:545-552
15. Baumgartner H, Hung J, Bermejo J, Chambers J B, Evangelista A, Griffin B P, lung B, Otto C M, Pellikka P A, Quinones M. Echocardiographic assessment of valve stenosis: Eae/ase recommendations for clinical practice. *J Am Soc Echocardiogr.* 2009; 22:1-23; quiz 101-102
16. Nishimura R A, Otto C M, Bonow R O, Carabello B A, Erwin J P, 3rd, Guyton R A, O'Gara P T, Ruiz C E, Skubas N J, Sorajja P, Sundt T M, 3rd, Thomas J D. 2014 aha/acc guideline for the management of patients with valvular heart disease: A report of the American college of cardiology/american heart association task force on practice guidelines. *J Am Coll Cardiol.* 2014; 63:e57-185
17. Cribier A, Eltchaninoff H, Bash A, Borenstein N, Tron C, Bauer F, Derumeaux G, Anselme F, Laborde F, Leon M B. Percutaneous transcatheter implantation of an aortic valve prosthesis for calcific aortic stenosis: First human case description. *Circulation.* 2002; 106:3006-3008
18. Faxon D P. Transcatheter aortic valve implantation: Coming of age. *Circulation.* 2011; 124:e439-440
19. Webb J, Cribier A. Percutaneous transarterial aortic valve implantation: What do we know? *Eur Heart J.* 2011; 32: 140-147
20. Smith C R, Leon M B, Mack M J, Miller D C, Moses J W, Svensson L G, Tuzcu E M, Webb J G, Fontana G P, Makkar R R, Williams M, Dewey T, Kapadia S, Babaliaros V, Thourani V H, Corso P, Pichard A D, Bavaria J E, Herrmann H C, Akin J J, Anderson W N, Wang D, Pocock S J. Transcatheter versus surgical aortic-valve replacement in high-risk patients. *N Engl J Med.* 2011; 364:2187-2198
21. Leon M B, Smith C R, Mack M, Miller D C, Moses J W, Svensson L G, Tuzcu E M, Webb J G, Fontana G P, Makkar R R, Brown D L, Block P C, Guyton R A, Pichard A D, Bavaria J E, Herrmann H C, Douglas P S, Petersen J L, Akin J J, Anderson W N, Wang D, Pocock S. Transcatheter aortic-valve implantation for aortic stenosis in patients who cannot undergo surgery. *N Engl J Med.* 2010; 363:1597-1607
22. Kutting M, Roggenkamp J, Urban U, Schmitz-Rode T, Steinseifer U. Polyurethane heart valves: Past, present and future. *Expert Rev Med Devices.* 2011; 8:227-233

23. Ladich E, Nakano M, Virmani R. Pathologic findings in aortic stenosis. In: Min J K, ed. *Muilimodality imaging for transcatheter aortic valve replacement*. London, UK: Springer; 2014:145-156.

(2) SPECIFIC DETAILS

This disclosure provides a novel polymeric valve whose leaflets possess calcium hydroxyapatite inclusions immersed in them. These valves can be produced to replicate different grades of calcification (e.g., mild, moderate or severe) to test transcatheter aortic valve implantation in vitro or even in vivo.

Currently there is no large animal model with natural calcified heart valve or vessel, and lack of such an animal model makes the research and development studies related to cardiovascular devices very difficult. Many devices, such as but not limited to transcatheter heart valve repair/replacement technologies, require a calcified heart valve in animals to show their feasibility. However, so far, such an animal model does not exist. This invention describes polymeric valve and vessels to be implanted in animals or used in vitro prior to implantation/use of a developed technology within, and a method to make them with a controlled level of immersed calcium appetite inclusions. Calcium inclusion within the thickness of the valve or vessel provides opportunity to visualize the valve with a variety of imaging modalities such as x-ray, CT scan, fluoroscopy, and ultrasound. It also provides an environment inside the body that replicates calcifications in human cardiovascular system, once implanted inside the animal. The animal that receives this calcified valve/vessel can then be used as a model of calcified valve/vessel for other technologies to be tested in.

In other words, the calcified polymeric valves and vessels described herein are generated to be calcified inclusions. The valves or vessels (vascular segments) are then implanted in a live animal (such as a sheep or pig) for a period of time, such as a second, hour, day, week, etc. Thereafter, a secondary device, such as a stent or deployable heart valve can be inserted into the live animal and the calcified valve, vessel, etc., to allow for testing of the secondary device. In this aspect, this allows for testing of the second device in what are likely real world conditions where the actual human subject does not possess a perfect valve or vessel and, instead, likely has a calcified valve or vessel. It should be understood that the calcified polymeric valve or vessel can also be inserted or implanted into a laboratory working heart or other laboratory equipment to simulate a real world environment for testing of the secondary device. The performance of these valves were studied in vitro using a simulator as described in further below.

(2.1) Calcific Valve

Figure 2:
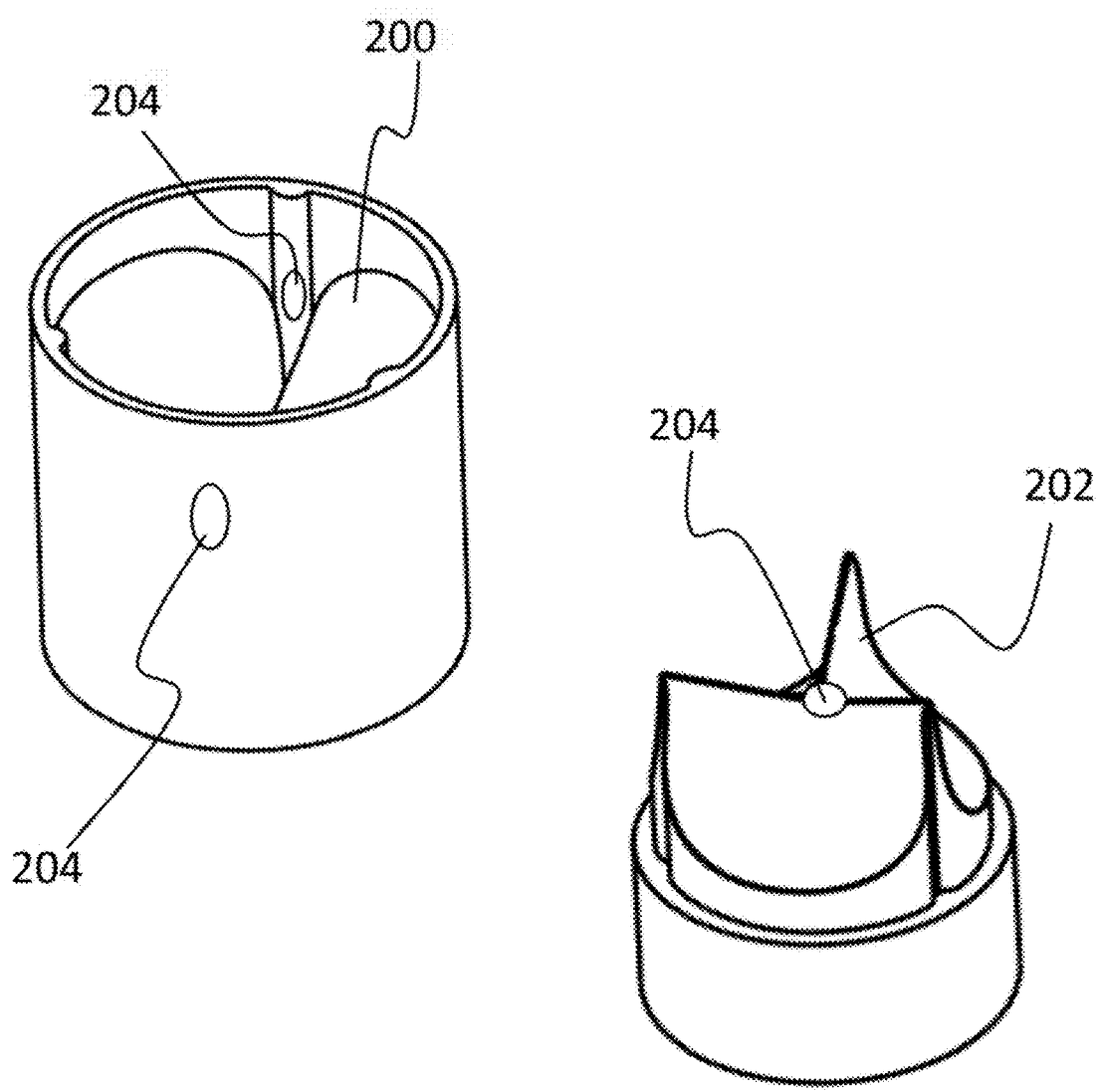
FIG. 2 is an illustration depicting female and male silicon molds as made for casting according to various embodiments of the present invention.
Figure 3:
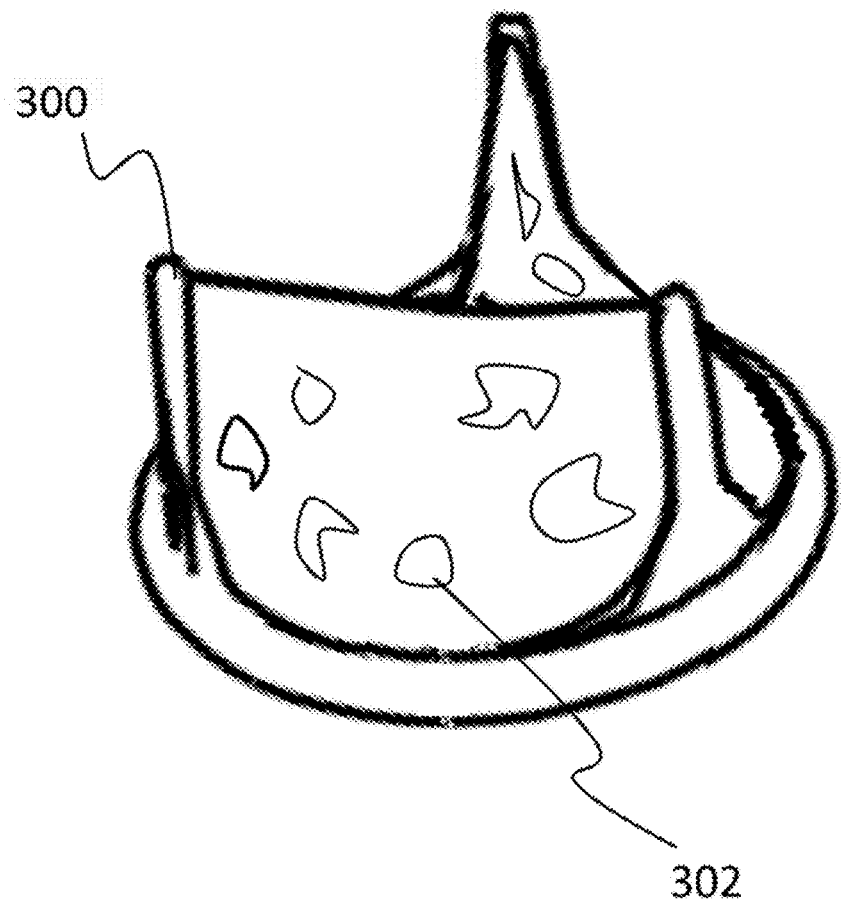
FIG. 3 is an illustration of a calcified valve with calcium inclusions according to various embodiments of the present invention.

This disclosure provides a calcified polymeric valve and a method for making such a valve. It should be understood that any suitable method for forming such a valve can be employed, so long as the resulting valve possesses calcified inclusions. A non-limiting example of such a method includes the following steps or acts.

a. As shown in FIG. 1, a male 100 and female 102 piece of the heart valve is made. This can be formed of metal or any other suitable rigid material, including clay, ceramic, etc.

b. Using the male 100 and female 102 pieces, corresponding female 200 and male 202 silicon molds (as shown in FIG. 2) are made for casting. For example, the male 100 and female 102 pieces can be positioned into silicon to generate the corresponding female 200 and male 202 silicon molds. The female 200 and male 202 silicon molds provide space for material, such as polyurethane, being casted in between.

c. The mold (i.e., collectively the female 200 and male 202 mold parts) is then filled with the casting material (e.g., polyurethane) using different holes 204 and funnels within those male 202 and female 200 silicon molds.

d. The casting material can be mixed to generate desired hardness, color and viscosity. The casting material is ideally de-bubbled using a vacuum pump to ensure the consistency of the material after casting. In other words, after pouring the casting material into the molds (i.e., between the female 200 and male 202 mold parts), the molds are put in a pressure chamber to minimize any bubble in the structure (eliminates bubbles).

e. A second layer of polyurethane mixed with calcium phosphate is then injected over the first layer to mimic the calcified spots. The same de-bubbling processes as listed in Step # d above can be applied to the second layer cast. More layers can be applied to the cast, as required.

f. Finally, the molds will be taken apart and the formed valves can be removed from the molds, resulting in a calcified valve (or vessel) 300 with calcium inclusions 302 (as shown in FIG. 3).

Figures 4A, 4B, 4C:
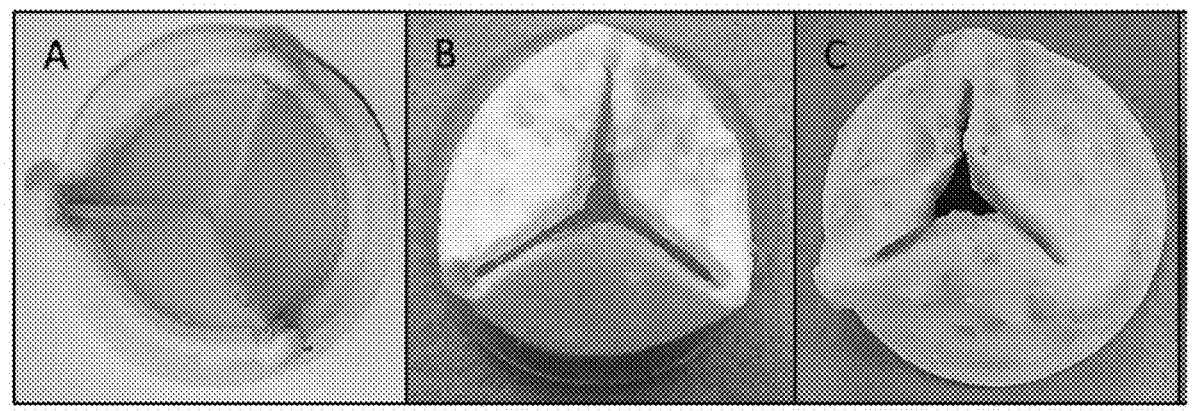
FIG. 4A is an illustration of a control valve.
FIG. 4B is a moderately-stenotic calcified polymeric valve.
FIG. 4C is an illustration of a severely-calcified polymeric valve.

It should be understood that the process described above can be applied to both heart valves and vascular segment (vessels) to generate the resulting valves or segments having calcium appetite inclusions immersed therein and/or thereon. For experimental purposes and to demonstrate valves generated as a result of the process described herein, models of calcified aortic valves with moderate and severe stenosis were created, shown in FIGS. 4B and 4C, respectively. In these examples, a mixture containing calcium phosphate $Ca_3(Po_4)_2$ was developed to replicate calcified nodules on the valve leaflets. The mixture was based on ¼ ounce $Ca_3(Po_4)_2$ and ⅛ of ounce Polyurethane (as obtained from BJB Enterprises, located in Tustin, Calif.). ⅛ ounce and ¼ ounce of the mixture were used to develop moderately- and severely-stenotic valves, respectively. To make the valve, the mixture was applied layer-by-layer and then was set inside a Silicone mold. After several trial and error attempts, a proper mold for each part was made. The process of mixing, pouring, curing and demold time took about eight hours. Molds were manually made according to anatomical figures of a native calcified aortic valve. Custom made molds for each level was made by Silicone Rubber with a hardness shore of 30 A and a tensile strength of 700 PSI, with a mixing ratio by part A 100% and part B 10%. The two-part mold was set to develop the aortic valve of size 23 mm. Thickness of the calcium-phosphate mixture specify the level of calcification and accordingly grade of stenosis. The resulting moderately- and severely-calcified stenotic valves are shown in FIGS. 4B and 4C, respectively. As noted above, the performance of these valves were studied in vitro using a simulator as described below.

(3) EXPERIMENTAL RESULTS

(3.1). Heart Flow Simulator

Figure 5:
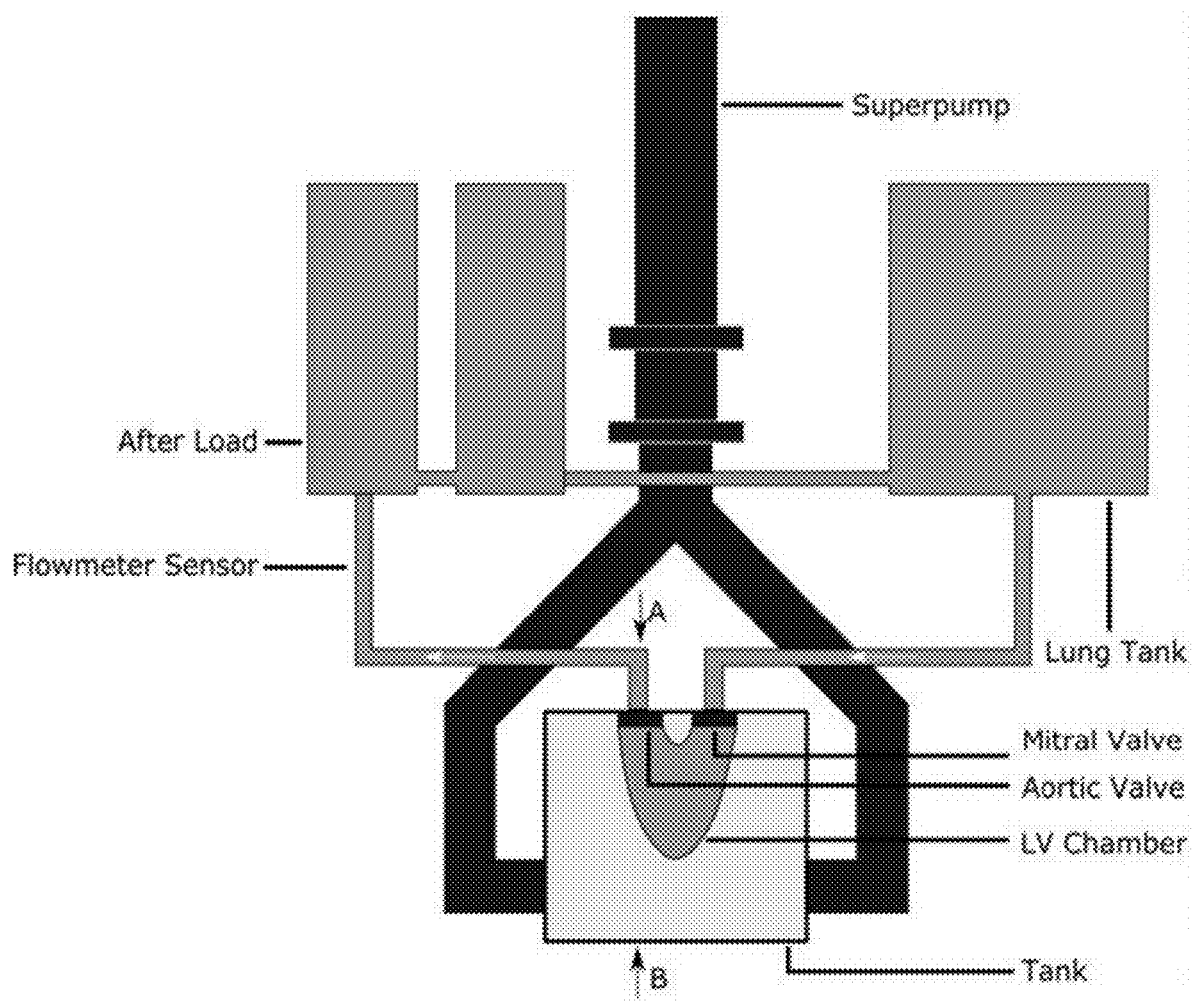
FIG. 5 is an illustration of a heart flow simulator as used as an experimental setup.

A heart pulsed flow simulator was used to test the developed calcified valves. The heart pulsed flow simulator is the same as that as previously described in Literature Reference Nos. 11-14. The system's modular build allows addition of transparent patient-specific ventricles. The ventricular sac is suspended over the Plexiglas atrium, free-floating inside a rigid water-filled container. The system is connected and actuated by a pulsatile pump system (such as the Superpump system, VSI, SPS3891, as developed by Vivitro systems Inc., Victoria, BC, Canada), which operates based on a VSI Wave Generator VG2001 (developed by Vivitro Systems Inc., Victoria, BC, Canada) and controlled by a customized interface according to predefined functions. The circulatory flow is periodically pulsatile, and is generated as the ventricular sac's response to input waveforms (FIG. 1). Water along with echocardiographic contrast agent (e.g., Optison™ as developed by GE Healthcare Inc., Princeton, N.J.) was used as the circulating fluid since the effect of blood viscosity was not a focus of this study. An example illustration of the simulator setup is depicted in FIG. 5, with A and B denoting the position of the 4V-D GE probe used for echocardiographic studies.

(3.2) Ventricular Model

A transparent ventricular model with adult dimensions at a systolic state was used for this study. The model is made of transparent silicone rubber and was placed in the circulatory system connected to the inlet and outlet tubes.

(3.3) Heart Valve for Mitral Position

For the mitral position, a 25 mm St. Jude bioprosthetic mitral valve (as developed by Biocor, St. Jude Medical Inc., St Paul, Minn.) was used.

(3.4) Models of Aortic Valves

A control and two calcific polymeric valves were used at the aortic position. For example, the control was a 23 mm CEP PERIMOUNT Theon PSR pericardial bioprosthesis (Edwards Lifesciences, Irvine, Calif.; FIG. 2A). This was considered to be the control valve for the study, with no calcification.

(3.4.1) Transcatheter Aortic Valve

Figures 4D, 4E:
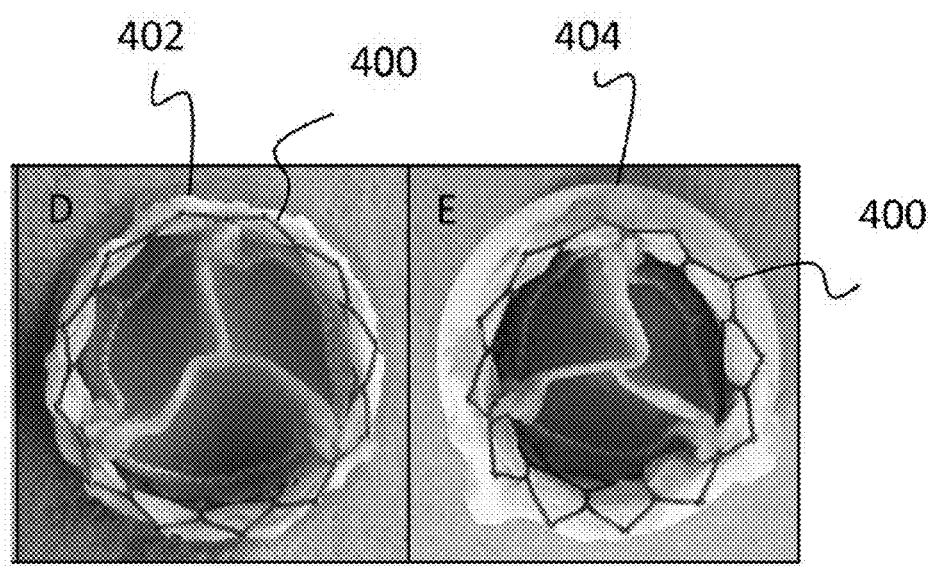
FIG. 4D is an illustration of a typical stented valve as positioned in a moderately-calcified valve.
FIG. 4E is an illustration of a typical stented valve implanted within a severely-calcified valve.

A transcatheter aortic stented valve was used to perform the valve-in-valve procedures. Specifically, as a non-limiting example, a FoldaValve™ (developed by FOLDA LLC, Rancho Santa Margarita, Calif.), which is a 14 Fr transcatheter aortic valve (TAV) that expands to 25 mm, was used to perform the valve-in-valve procedures. A stented valve in this example is a self-expandable aortic valve that uses a nitinol stent and bovine pericardial leaflets. (see, for example, Literature Reference No. 7). FIGS. 4D and 4E depict the stented valve 400 as implanted with a moderately-calcified valve 402 a severely-calcified valve 404, respectively.

(3.5) Experimental Conditions

Five sets of experiments were performed to replicate the use of a calcified aortic valve. Specifically, tested were the control aortic valve, a moderately-stenotic calcified valve, and a severely-stenotic calcified valve with or without a deployed stented valve implanted within. Flow conditions for all the experiments were set to 70 beats per minute under physiological waveforms that reproduce the desired Systolic Ratio (SR) of 35% for the LV model; SR is the fraction of time in a cardiac cycle that the LV is in systole (see Literature Reference No. 14).

(3.6) Aortic Valve Area Analysis

Motion of the aortic valve leaflets during the cardiac cycle was recorded by a video camera for all the experiments. Subsequently, the maximum aortic valve area during peak systole was calculated by image processing.

(3.7) Echocardiographic Studies

Figure 6:
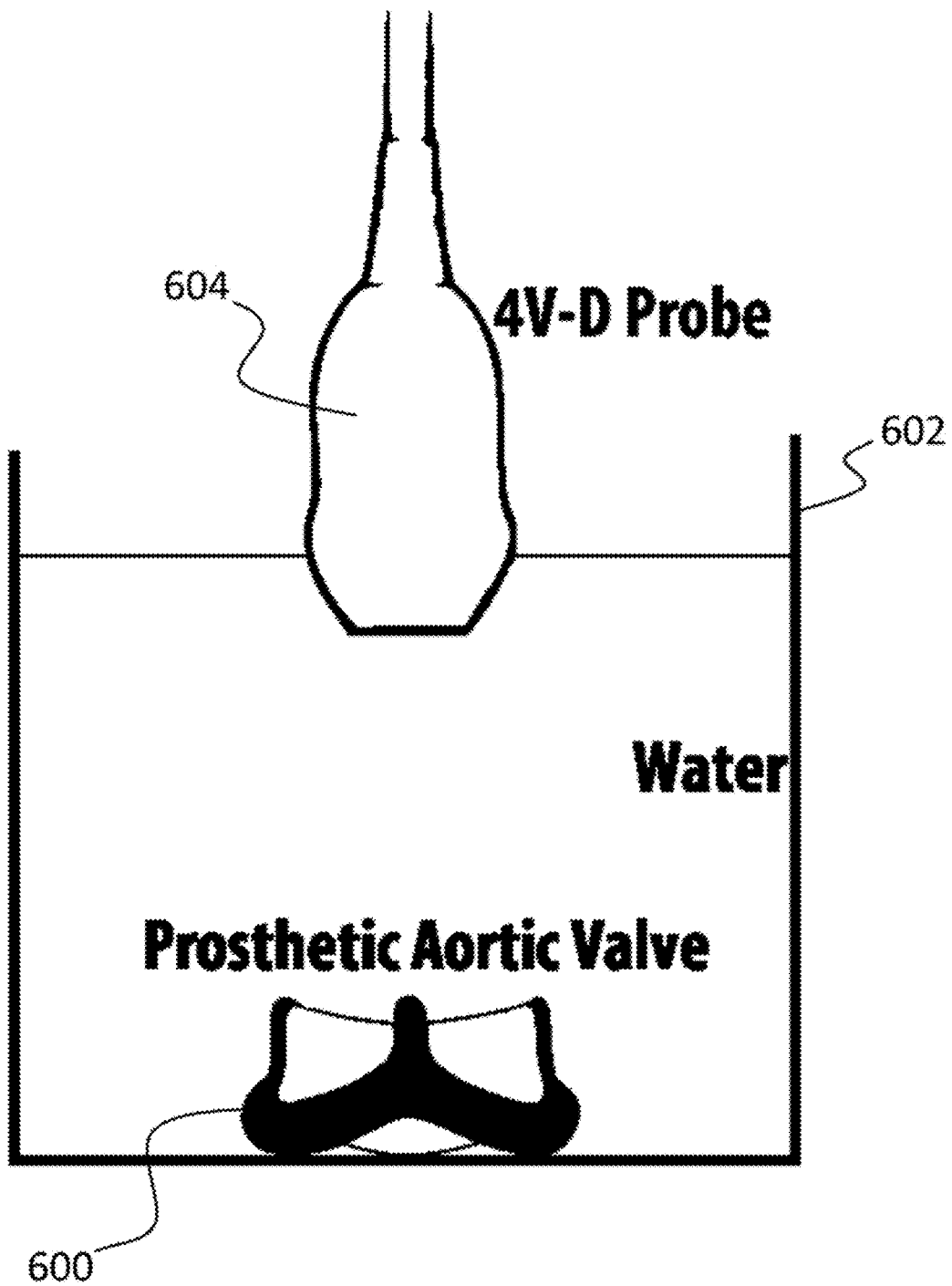
FIG. 6 is an illustration depicting a schematic of three-dimensional (3D) structural imaging of an aortic valve model.

A GE Vivid E9 echocardiography system (developed by GE Healthcare, Milwaukee, Wis.) was used to perform two-dimensional (2D) B-mode imaging, continuous wave Doppler echocardiography, 2D color Doppler and three-dimensional (3D) structural imaging. A schematic of the 3D structural imaging of the aortic valve models is depicted in FIG. 6. The valves 600 were immersed in a tank 602 filled with water. A 4V-D probe 604 was used to statically image the valve's 600 structure in 3D. The structural imaging was performed at two different positions (1) close to the tip of the leaflet and (2) near the middle of the valve. The acquisitions were performed by a 4V-D GE ultrasound transducer from two different positions: one distal to the aortic outflow and at the apex of the ventricular sac (labeled A and B in FIG. 5) to obtain both outflow and inflow views of the valve. Optison™ was used as the contrast agent to improve the flow echogenicity.

(3.8) Results (3.8.1) Calcified Aortic Valves

For this study and as illustrated in FIGS. 4B and 4C, two polymeric valves of 23 mm with randomly distributed hydroxyl-appetite inclusions were made to replicate a severely-stenotic and moderately-stenotic aortic valve, respectively.

(3.8.2) Aortic Valve Area

FIGS. 7A through 7E illustrate the aortic valve area (AVA) of all the studied aortic valves. Specifically, FIGS. 7A through 7E illustrate a control valve, a moderately-stenotic calcified polymeric valve, a severely-calcified polymeric valve with a significant level of calcification, a stented valve implanted in moderately-calcified valve, and a stented valve implanted within a severely-calcified valve, respectively.

Figure 7A:
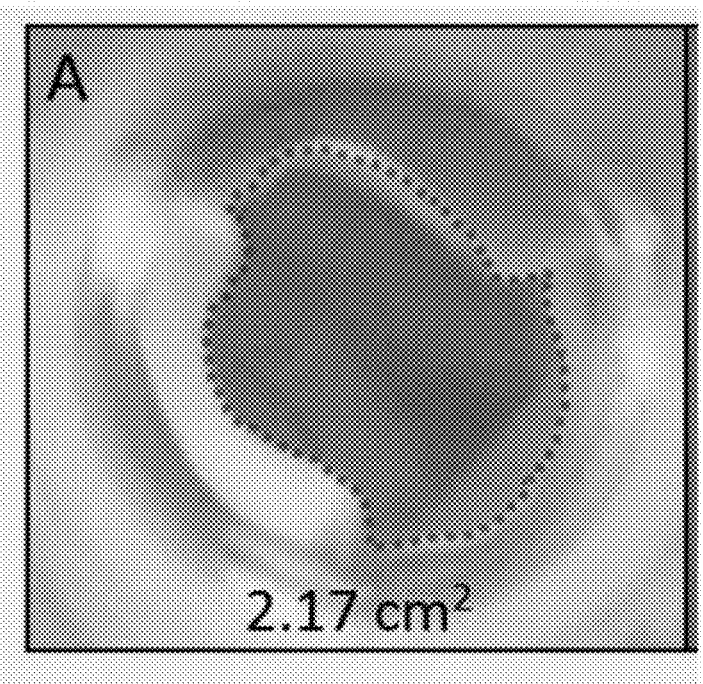
FIG. 7A is an illustration depicting aortic valve area (AVA) of a control valve.
Figure 7B:
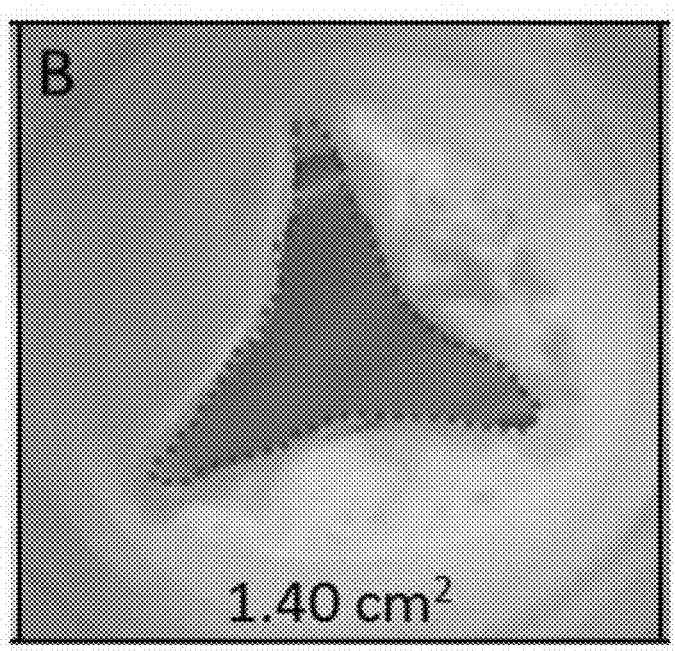
FIG. 7B is an illustration depicting the AVA of a moderately-stenotic calcified polymeric valve.
Figure 7C:
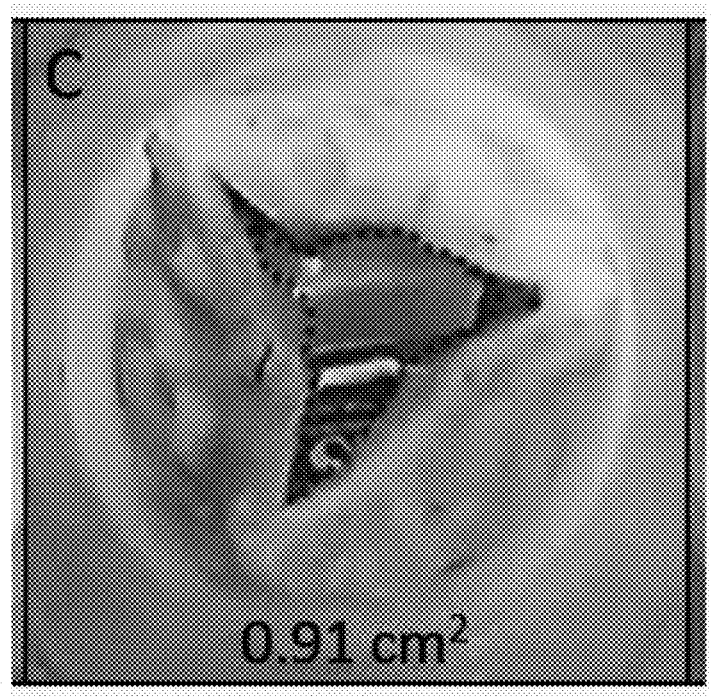
FIG. 7C is an illustration depicting the AVA of severely-calcified polymeric valve with significant level of calcification.
Figure 7D:
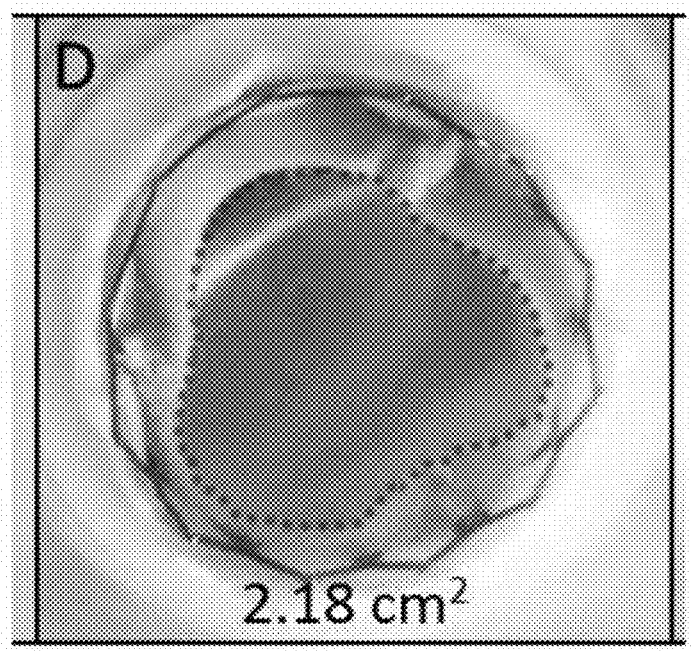
FIG. 7D is an illustration depicting the AVA of a moderately-calcified valve with an implanted typical stented valve.
Figure 7E:
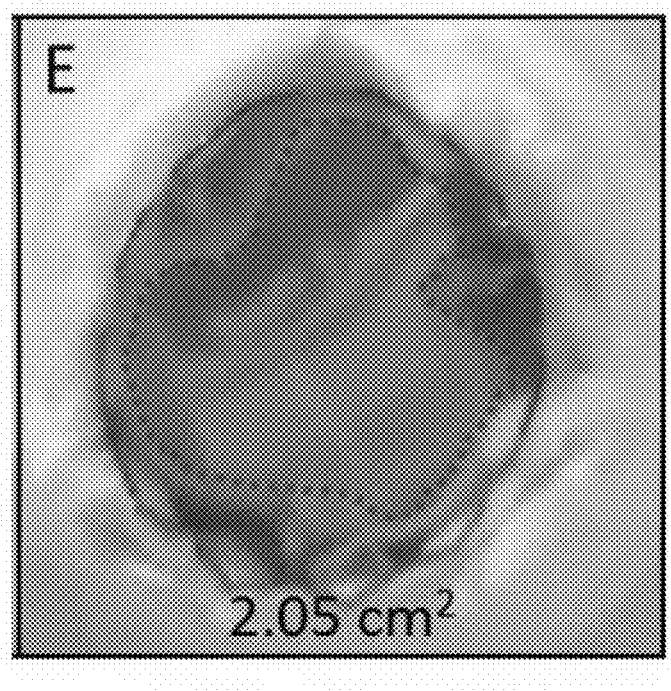
FIG. 7E is an illustration depicting the AVA of a severely-calcified valve with an implanted typical stented valve.

The moderately and severely-calcified valve's AVA (as shown in FIGS. 7B and 7C) were measured as 1.40 cm$^2$ and 0.91 cm$^2$, respectively, compared to the control valve (as shown in FIG. 7A) whose AVA was measured 2.17 cm$^2$. The stented valve was successfully deployed in the polymeric valves and calcium stayed intact on the leaflets of the polymeric valves with no calcium dislodgment being observed. After the deployment of the stented valve into the calcified valves (shown in FIGS. 7D and 7E), AVA was improved up to the level of the control valve's (2.18 cm$^2$ and 2.05 cm$^2$ for moderately and severely-calcified valve, respectively).

(3.8.3) 3D Structure Imaging

Figure 8A:
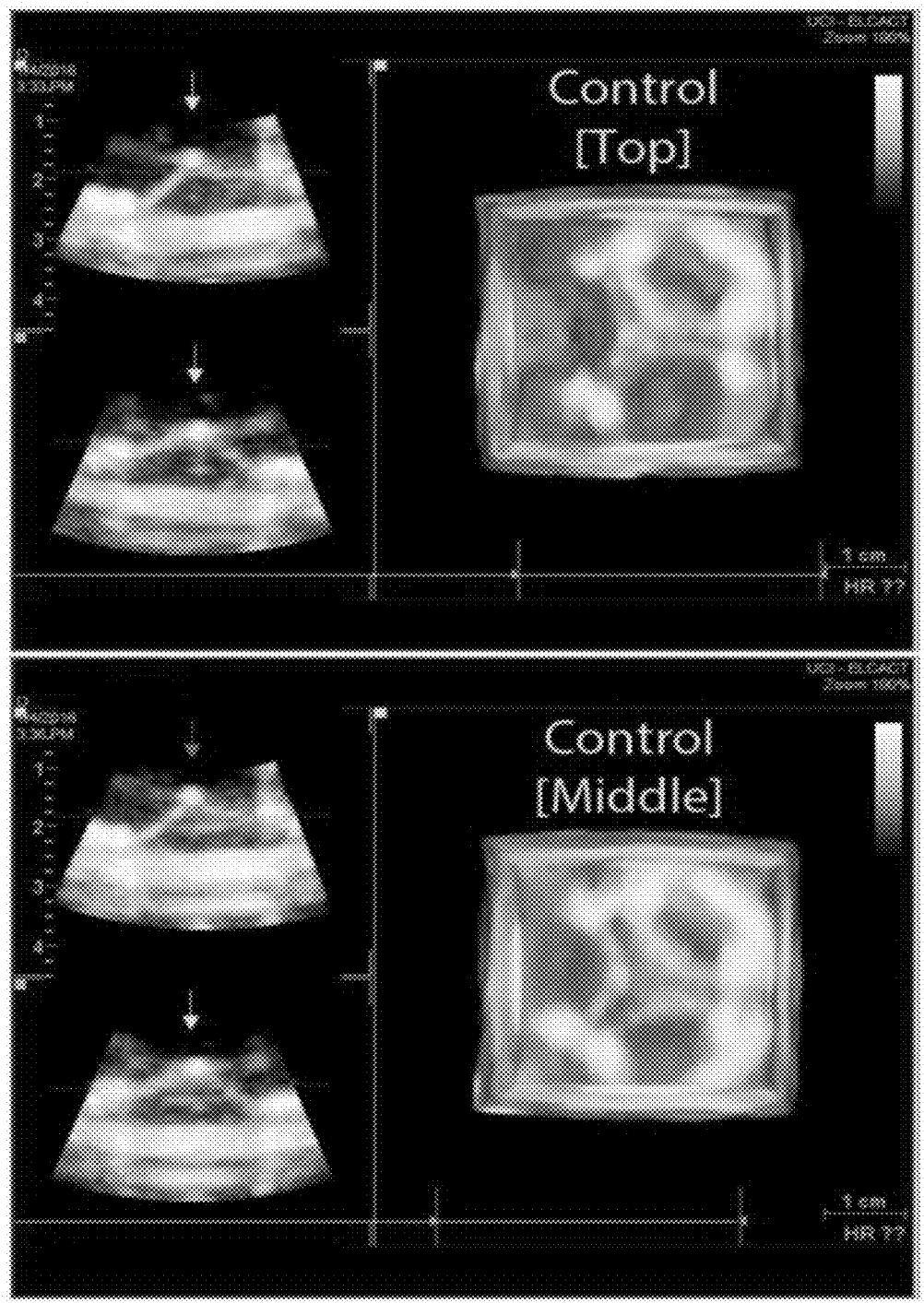
FIG. 8A is a 3D structural image for the control valve at two different positions, close to the tip and near the middle of the valve.
Figure 8B:
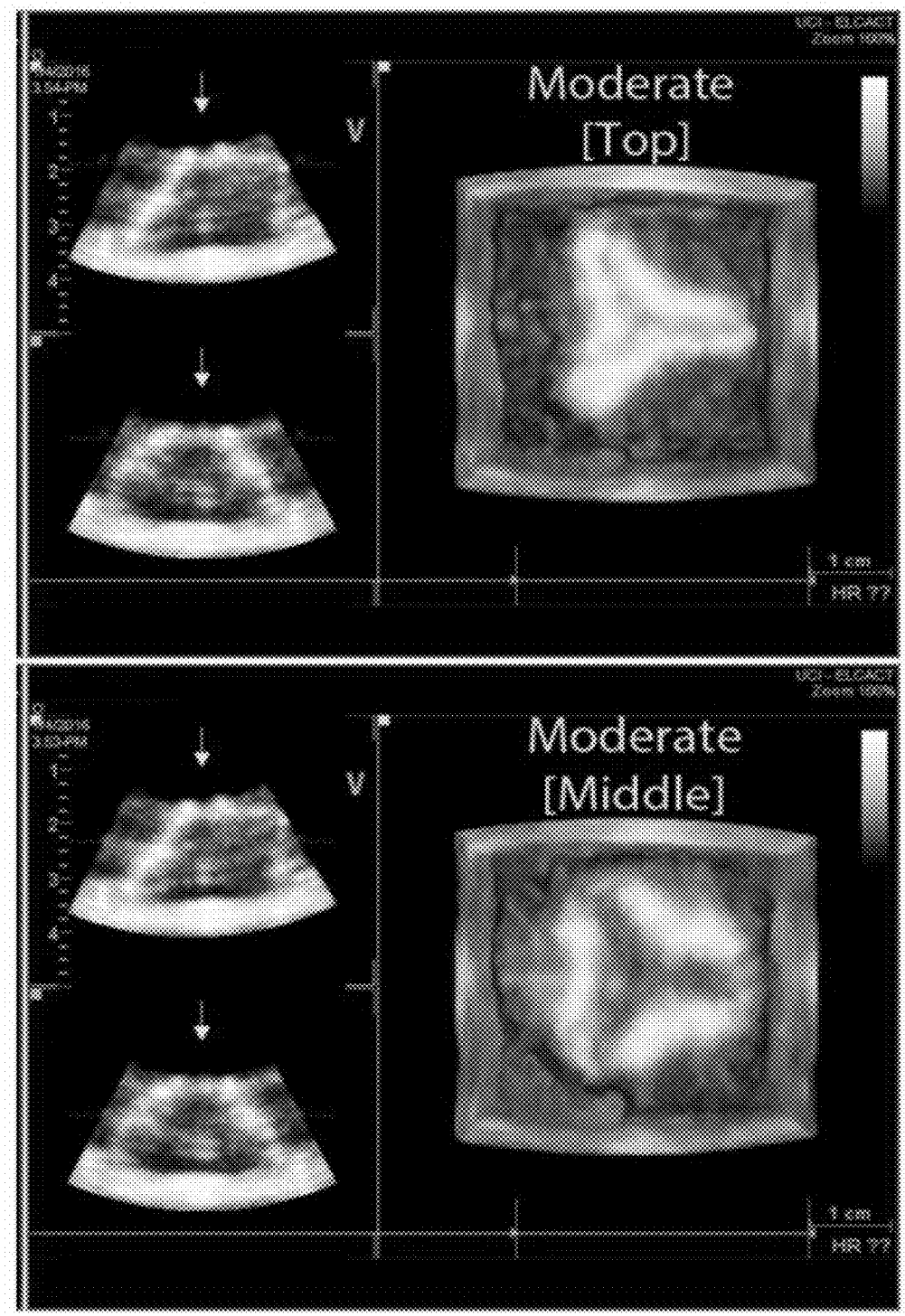
FIG. 8B is a 3D structural image for the moderately-calcified valve at the two different positions.
Figure 8C:
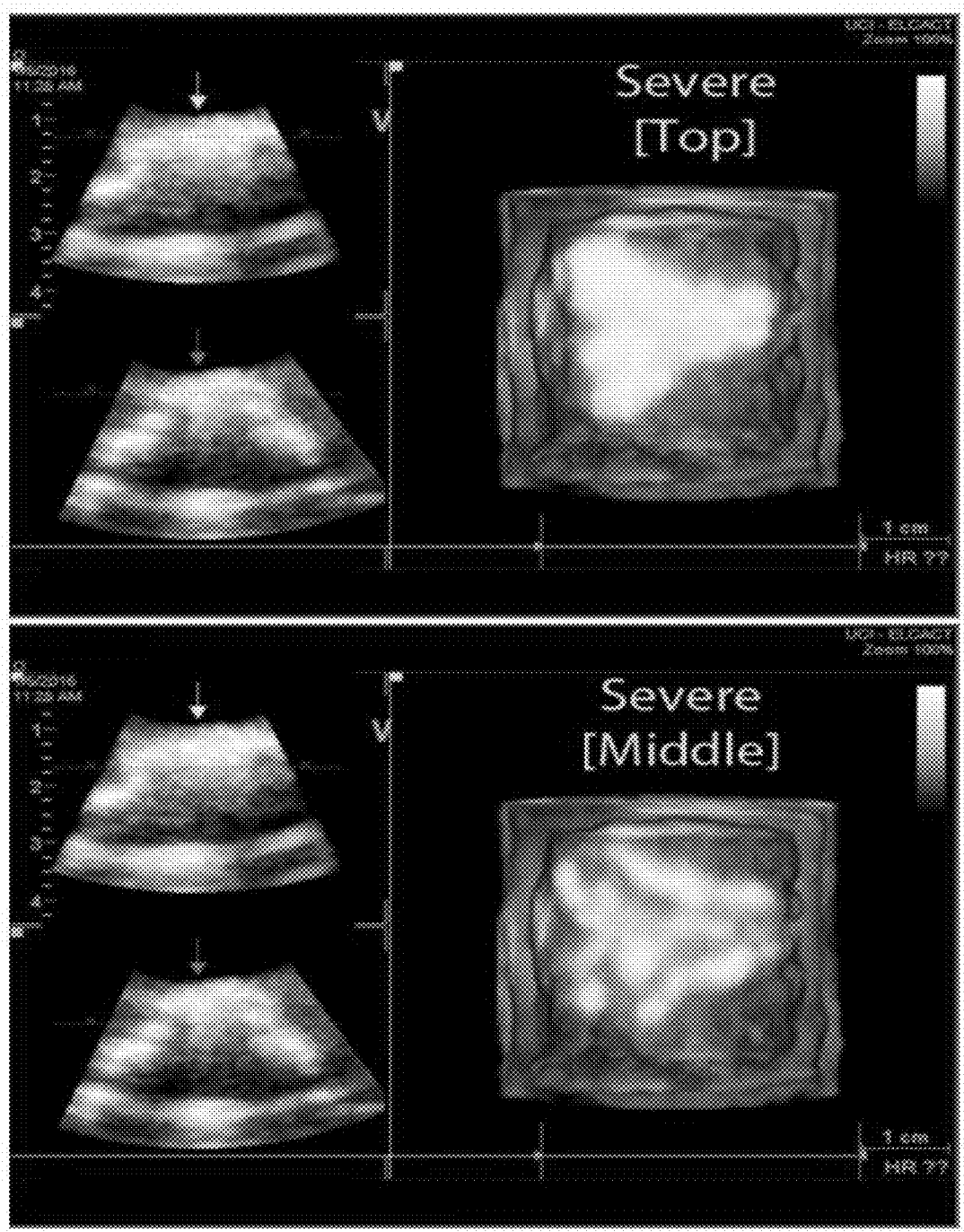
FIG. 8C is a 3D structural image for the severely-calcified valve at the two different positions.

The three-dimensional structure of the valve is shown in FIGS. 8A through 8C for the control, moderately-calcified, and severely-calcified valves, respectively, at two different positions close to the tip and near the middle of the valve. The high echogenicity over the leaflets were correlated to the degree of the calcification. Since the control valve (shown in FIG. 8A) does not have any calcified region, no high echogenicity region neither in vicinity of the tip nor in the middle of the valve's leaflets were observed. Alternatively, the regions of high echogenicity were observed in both moderately and severely-calcified valves (shown in FIGS. 8B and 8C, respectively). Compared to the control valve, these regions were larger and more prominent in both calcified valves. For the case of the severely-calcified valve, the echogenicities spread a larger area over the leaflets compared to the other valves, signifying the severity of the calcification and confirming the physical condition shown in FIG. 4C.

(3.8.4) Color Doppler Imaging

Figure 9A:
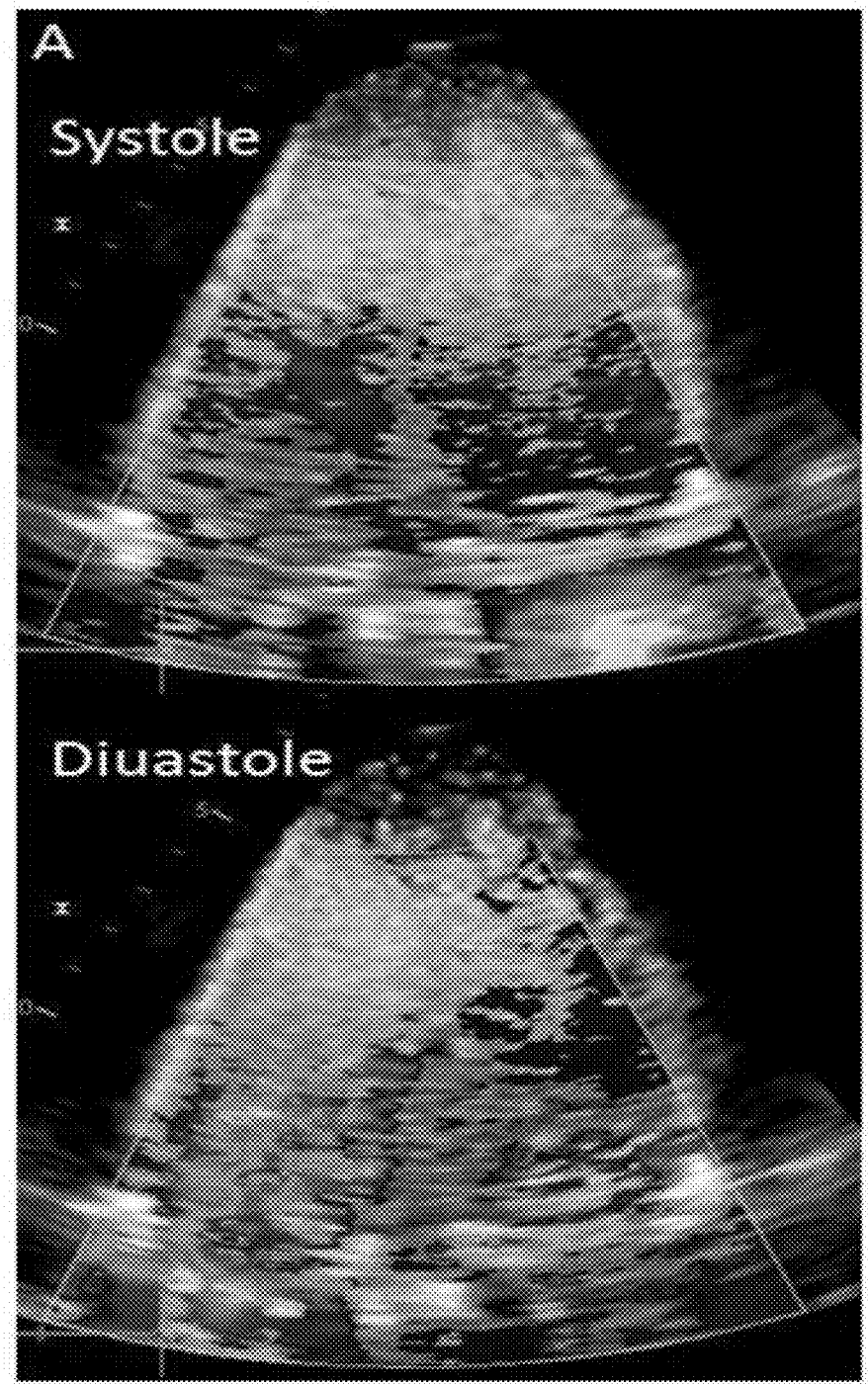
FIG. 9A are systole and diastole color Doppler images for the control valve.
Figure 9B:
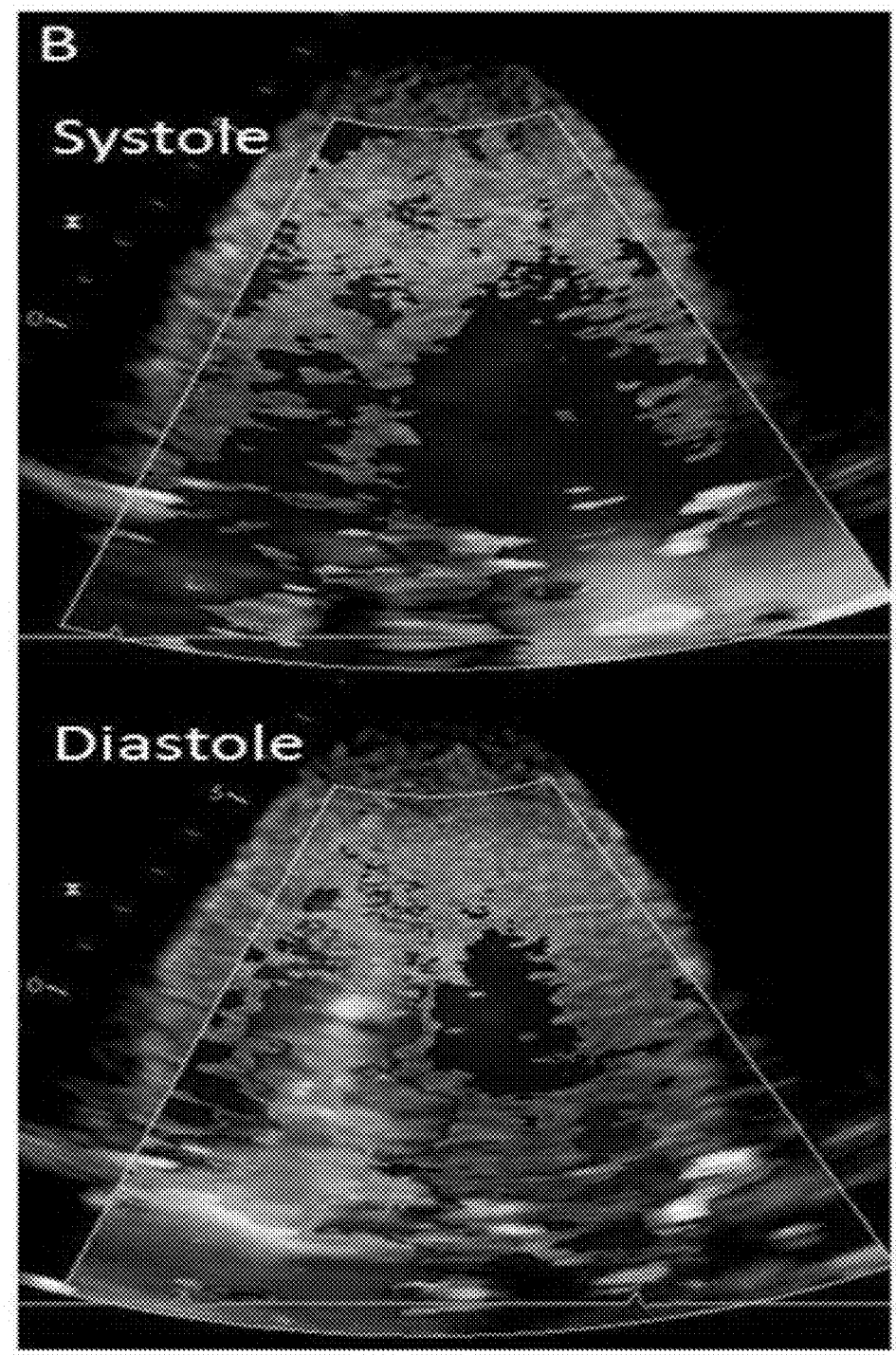
FIG. 9B are systole and diastole color Doppler images for the moderately-stenotic calcified polymeric valve.
Figure 9C:
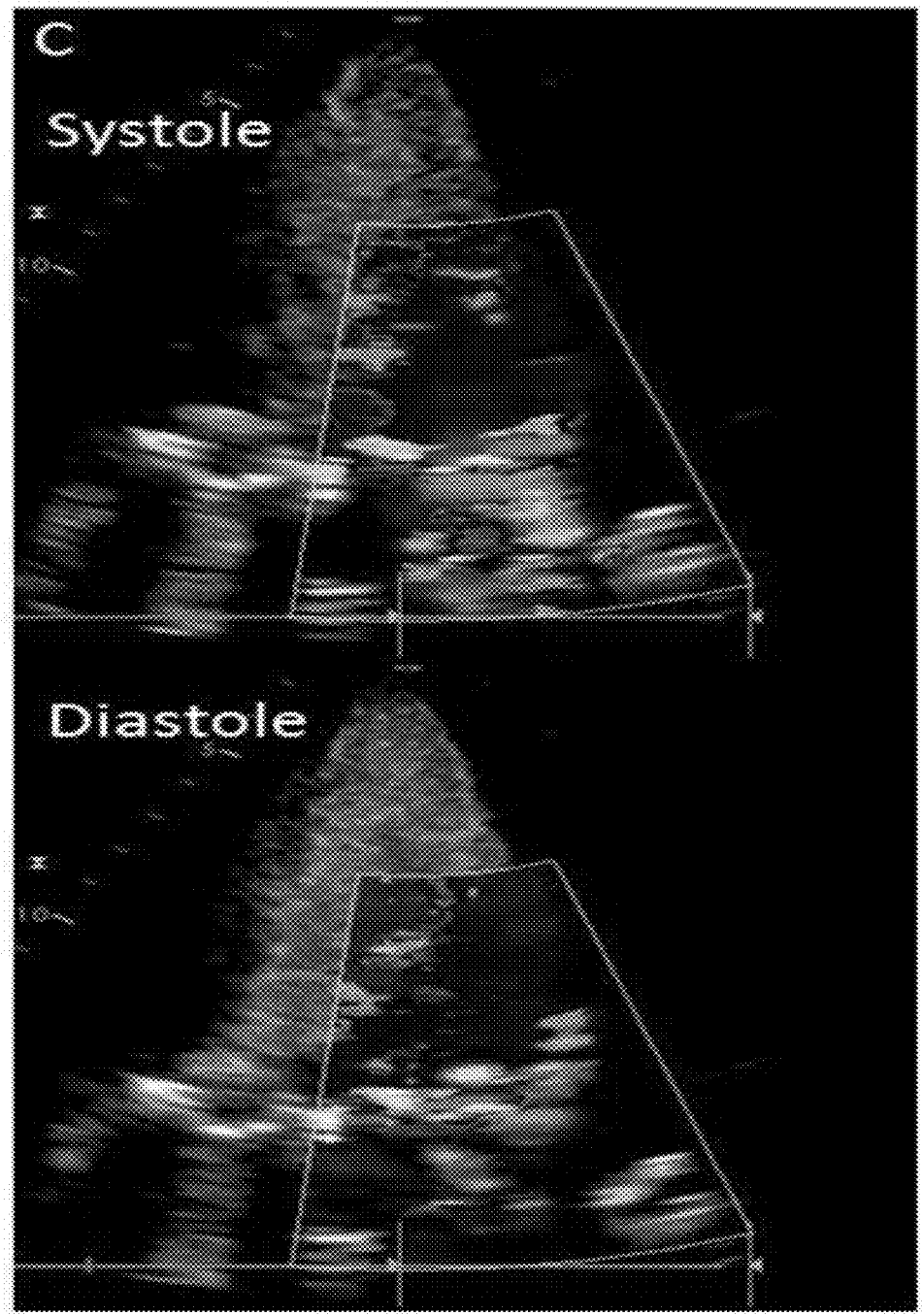
FIG. 9C are systole and diastole color Doppler images for the severely-stenotic calcified polymeric valve with significant levels of calcification.
Figure 9D:
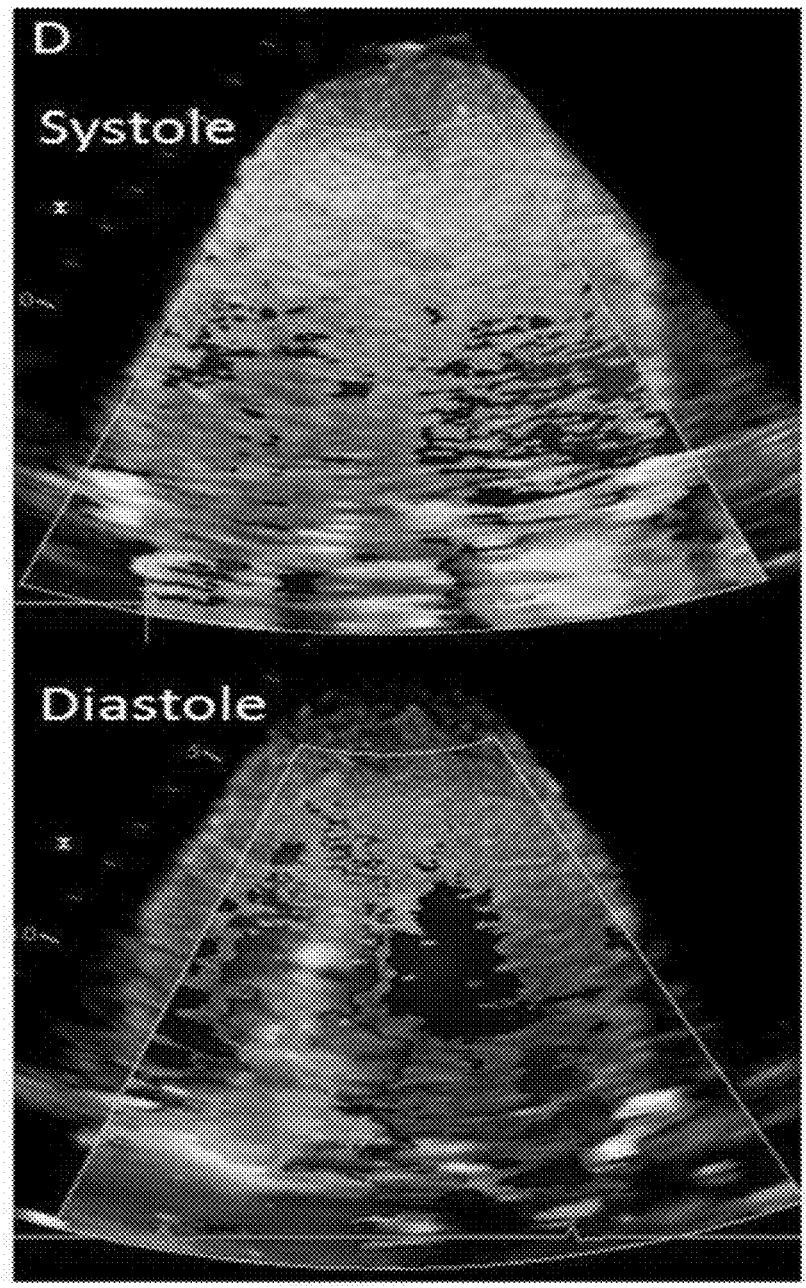
FIG. 9D are systole and diastole color Doppler images for the moderately-stenotic calcified polymeric valve with the implanted typical stented valve.
Figure 9E:
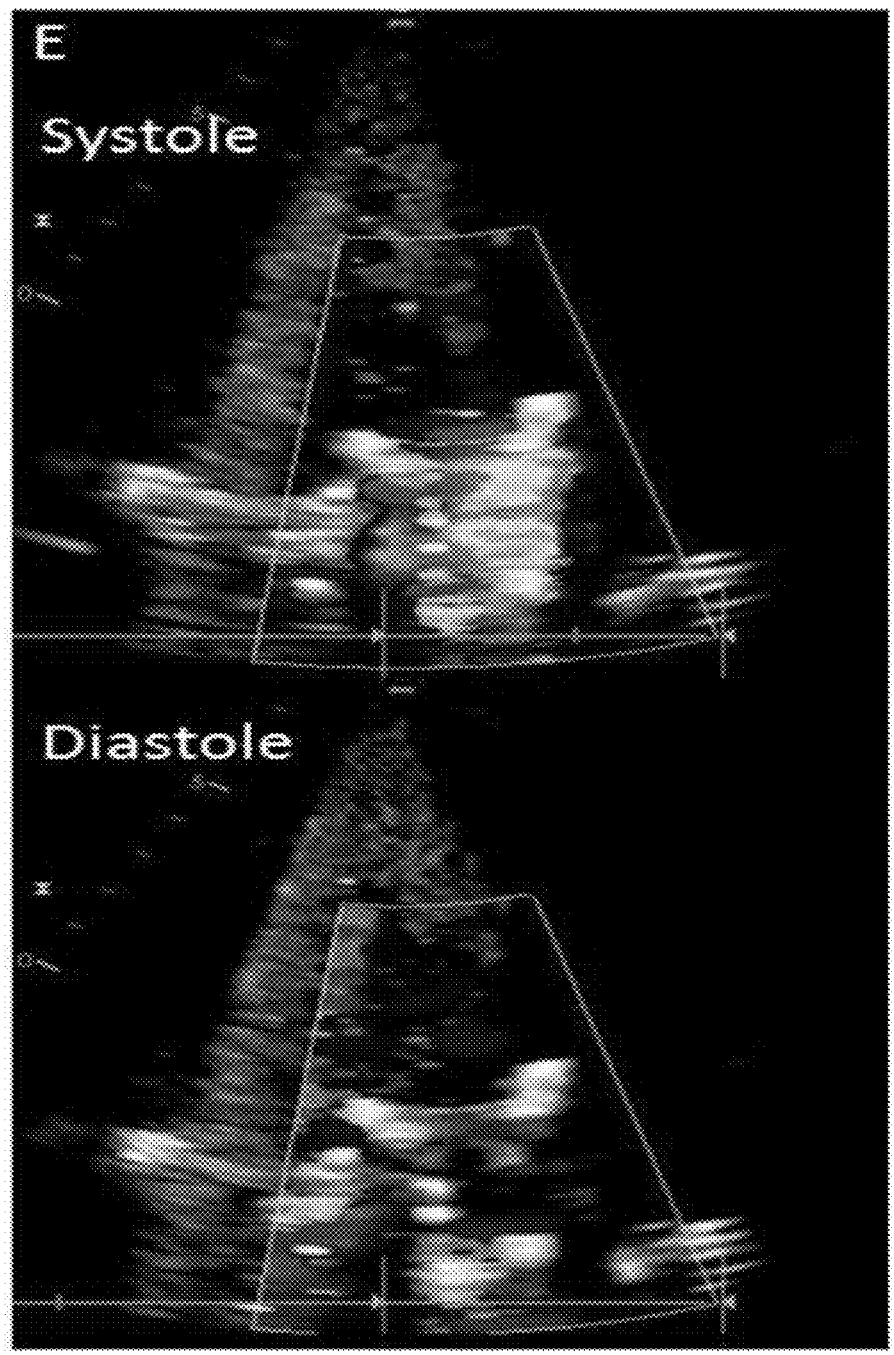
FIG. 9E are systole and diastole color Doppler images for the severely-stenotic calcified polymeric valve with the implanted typical stented valve.

Color Doppler imaging was performed to check the presence of the valve leakage. FIGS. 9A through 9E show Color Doppler images at peak-systolic and -diastolic phases. As anticipated, no obvious backward signal was observed in case of the control valve (shown in FIG. 9A). Alternatively, trivial backward signals were observed in severely-calcified valve (shown in FIG. 9C), but not observed in moderately-calcified valve (shown in FIG. 9B). After implanting the stented valve, the backward signal disappeared in both calcified valves (FIGS. 9D and 9E).

(3.8.5) Maximum Aortic Valve Jet Velocity

Figure 10A:
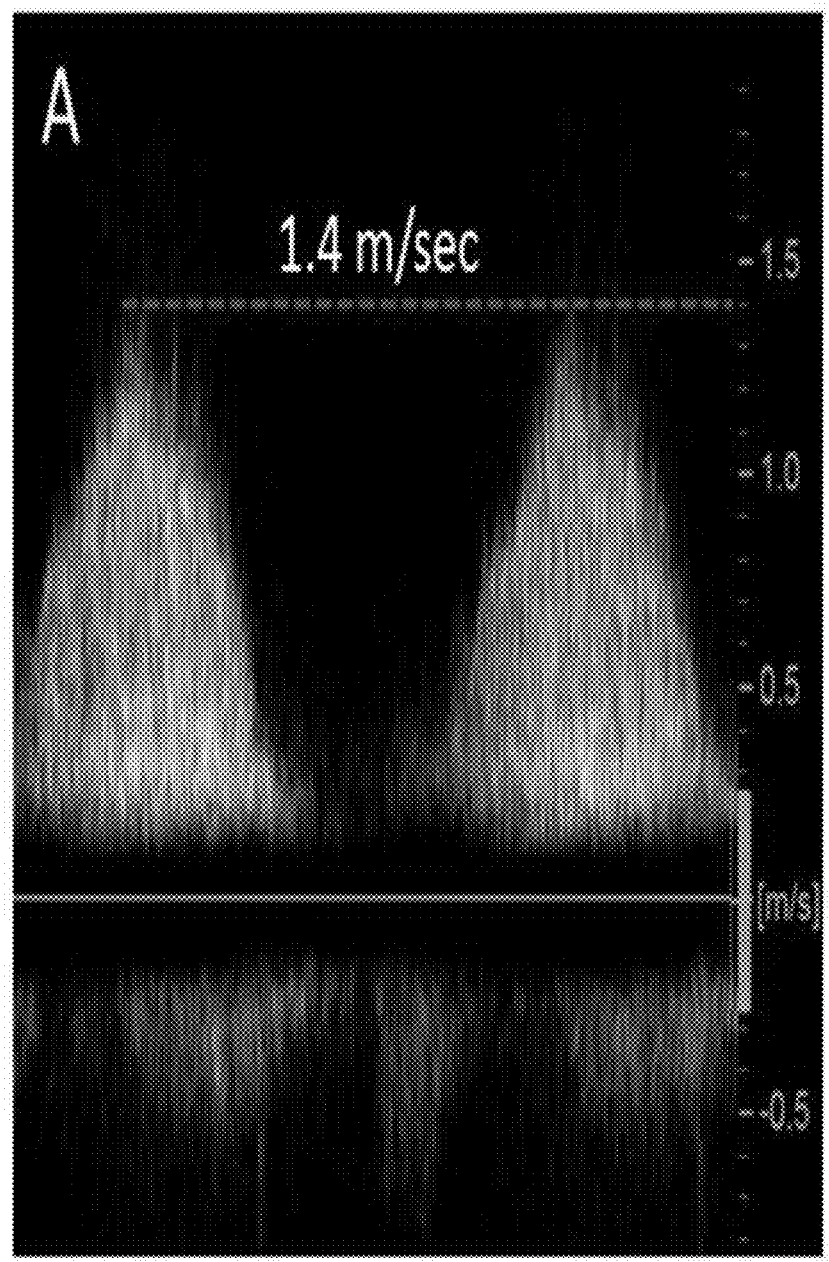
FIG. 10A is a continuous Doppler image for the control valve.
Figure 10B:
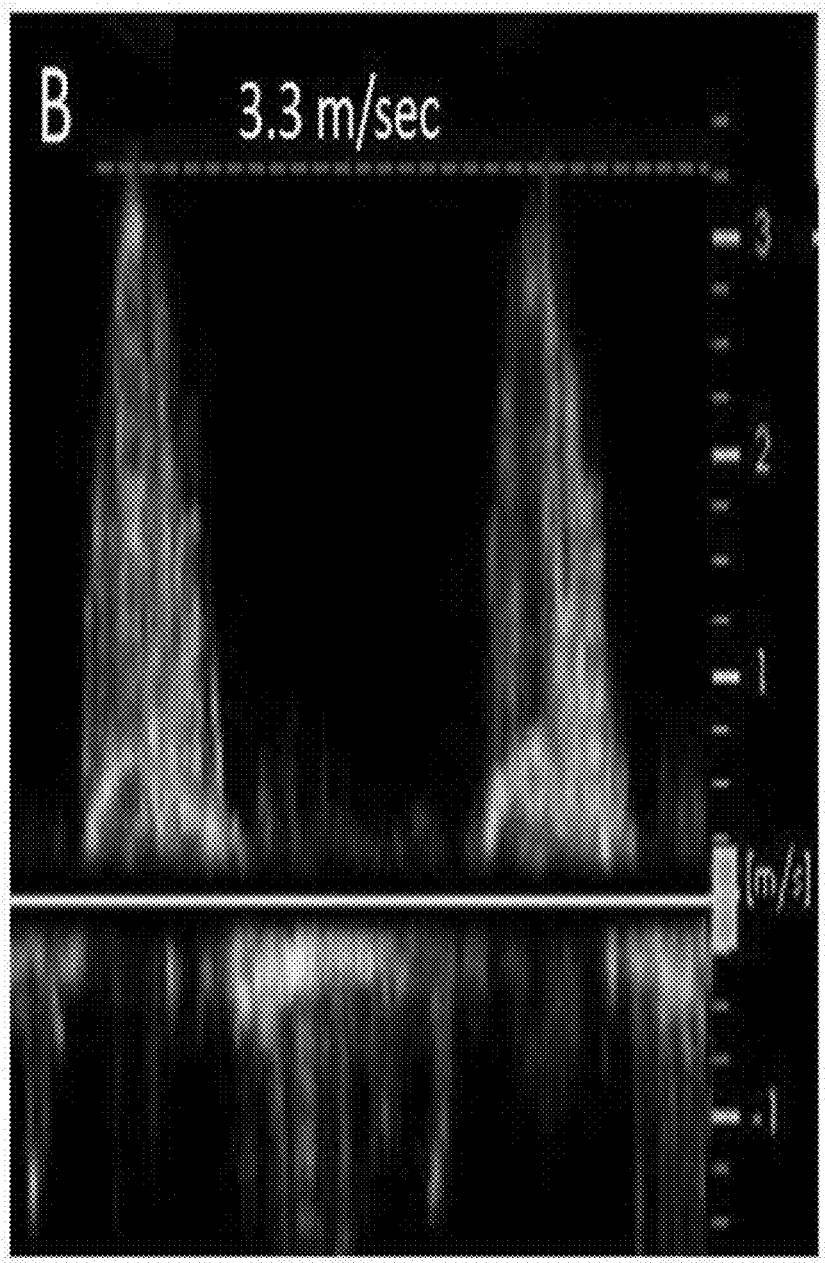
FIG. 10B is a continuous Doppler image for the moderately-stenotic calcified polymeric valve.
Figure 10C:
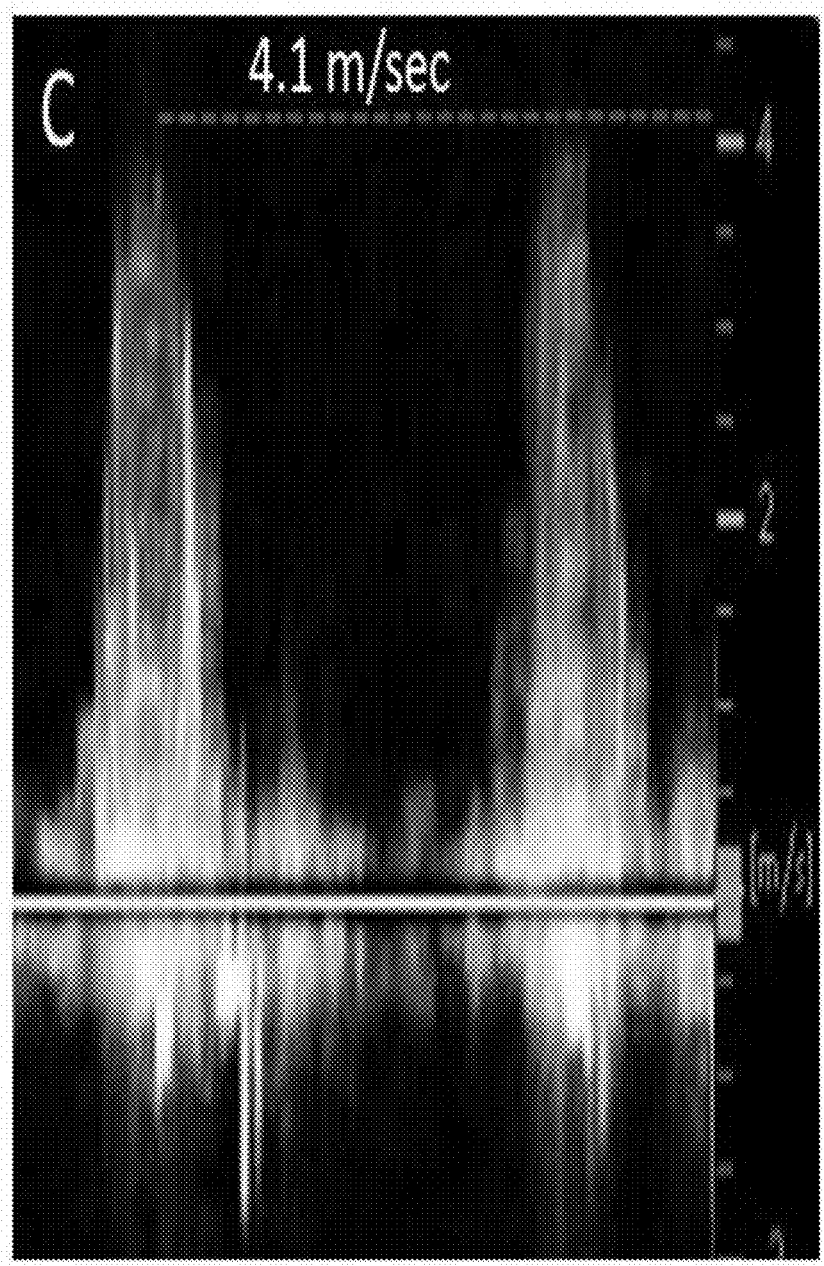
FIG. 10C is a continuous Doppler image for the severely-stenotic calcified polymeric valve with significant levels of calcification.
Figure 10D:
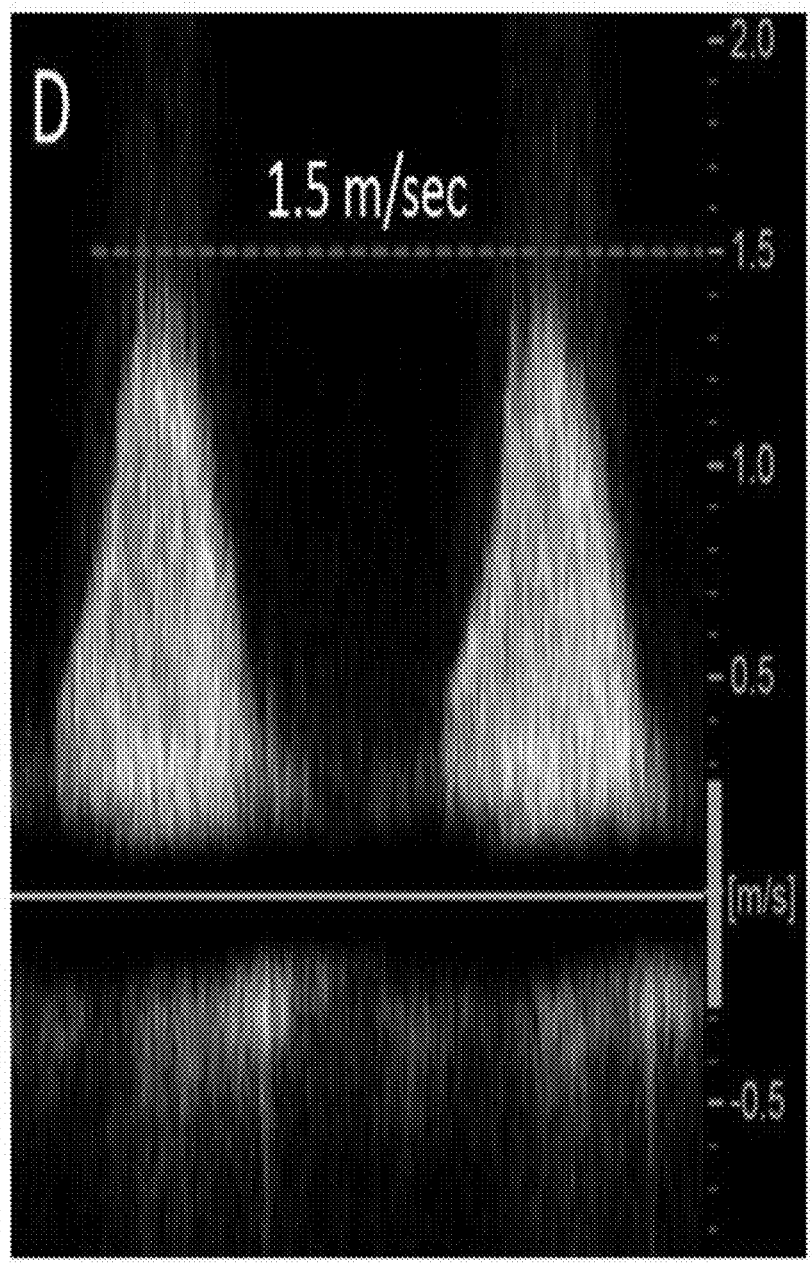
FIG. 10D is a continuous Doppler image for the moderately-stenotic calcified polymeric valve with the implanted typical stented valve.
Figure 10E:
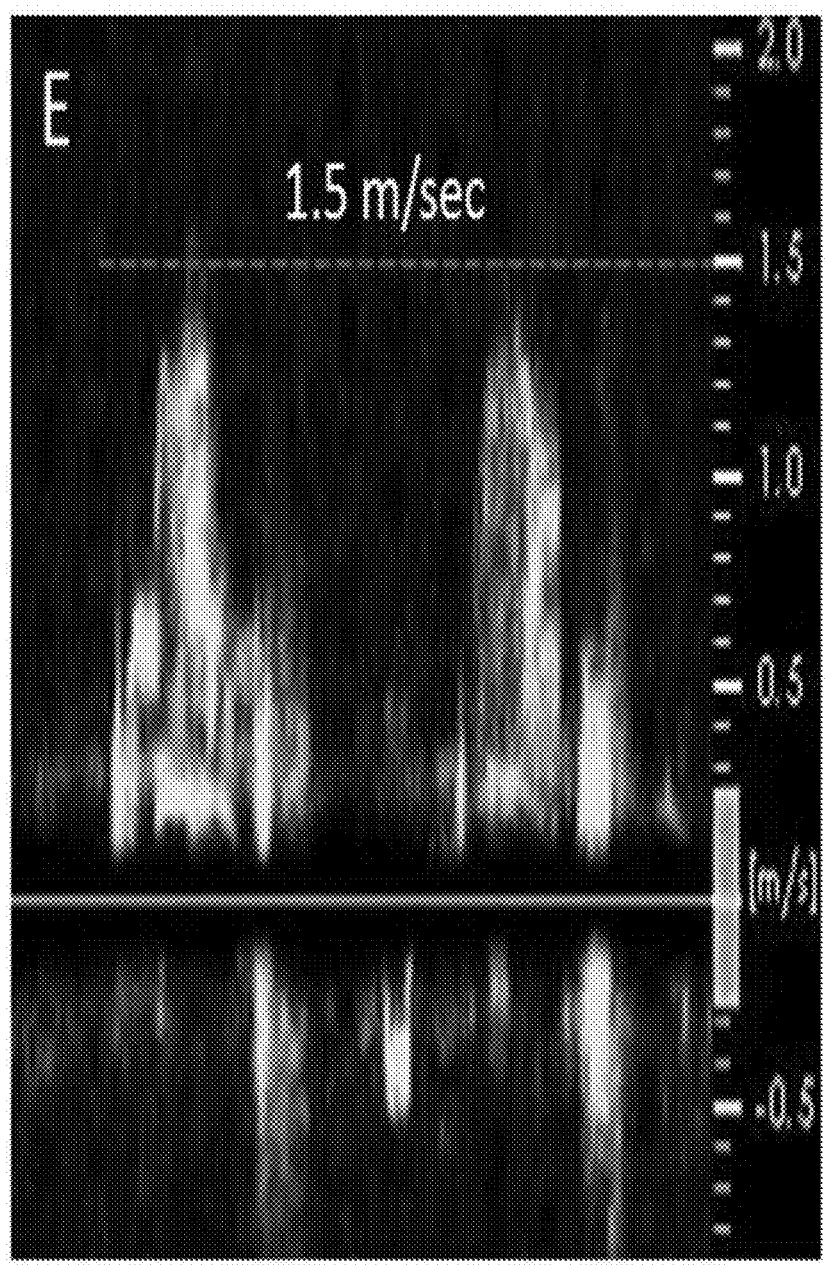
FIG. 10E is a continuous Doppler image for the severely-stenotic calcified polymeric valve with the implanted typical stented valve.

According to continuous wave Doppler images (shown in FIGS. 10A through 10E), the maximum aortic valve jet velocity of each aortic valve was measured. The peak jet velocity of the control valve (shown in FIG. 10A) was 1.4 m/sec, which is within the normal range of prosthetic valves. The significant elevation of peak jet velocity (3.3 m/sec) was observed in the moderately-calcified valve (shown in FIG. 10B). In addition, further elevation was observed in the severely-calcified valve (shown in FIG. 10C). Implantation of the stented valve canceled the elevation of maximum jet velocity in both calcified valves (shown in FIGS. 10D and 10E).

(4) DISCUSSION

As the aging society progresses, the prevalence of aortic valve stenosis is increasing. Although TAVR has been recently introduced, and the development of more advanced TAVR systems is enthusiastically progressing, no aortic valve stenosis model is yet available. Thus, this disclosure provides a polymeric valve with calcium hydroxyapatite inclusions to replicate a stenotic aortic valve.

(4.1) Severity of Aortic Valve Stenosis

The guideline of the American society of echocardiography (ASE) categorizes severity of aortic stenosis into three grades on the basis of AVA ($cm^2$) and maximum aortic valve jet velocity (m/sec). It the study described herein, the polymeric valves showed the restriction of valve opening and elevation of maximum aortic valve jet velocity. The calculated AVA and jet velocity were 1.40 $cm^2$, 3.3 m/sec and 0.91 $cm^2$, 4.1 m/sec in moderately and severely-calcified valves, respectively. Therefore, according to the ASE's guideline, the moderately and severely calcified valves are categorized into moderate and severe aortic stenosis. After deployment of the stented valve, aortic stenosis was improved back to the control level. These results indicate that the polymeric valves of this disclosure can accurately replicate different grades of aortic stenosis to test TAVR systems.

(4.2) Echocardiography and Valve's Echogenicity

In patients with aortic stenosis, echocardiographic examination is commonly performed to evaluate the severity of stenosis and calcification. In clinical practice, the high echogenicity of a native aortic valve generally indicates severe calcification. It was determined that the polymeric calcified valve (of this disclosure) showed higher echogenicity, compared with the control valve, and this echogenicity (represented by brightness) is associated with the degree of calcification (see FIGS. 9A through 9E). Accordingly, the polymeric calcified valve suitably replicated a natural calcified aortic valve as evaluated by echocardiography.

(4.3) Presence of the Regurgitation Based on Doppler Imaging

In the study described above, color Doppler imaging was obtained for all the experimental cases. In the polymeric calcified valve models, trivial degrees of regurgitation were observed using color Doppler imaging. These results indicate that this polymeric calcified valve not only can replicate the aortic stenosis but also aortic regurgitation.

(4.4) Clinical Implication

The number of TAVR procedures is increasing daily. Although many technical problems related to use of TAVR in high risk patients with aortic stenosis have been resolved, paravalvular leakage, valve durability, positioning accuracy, repositioning and retrieval are still considered clinical unmet needs (see Literature Reference Nos. 19-21). Therefore, in the near future, artificial heart valves mimicking valvular disease may play a more important role in the development of more sophisticated TAVR systems and improvement of the existing technologies. The polymeric calcified valve introduced here can be used for in vitro studies related to valve-in-valve applications. An advantage of this unique polymeric calcified valve is that the calcified surface of the valve leaflets can be custom-designed by controlling the amount and the location of calcium phosphate. The amount and location of calcium phosphate is controlled, for example, by replicating the shape of a particular native calcified valve by injecting calcium phosphate into the mold at the desired location and the desired amount. In addition, these valves can even be made or 3D-printed according to the patient-specific data acquired by CT-scan and/or echocardiography. Therefore, more precise clinical conditions can be replicated using these valves.

(4.5) Conclusion

This disclosure provides a polymeric calcified valve and a method for making the same. The study results provided herein also validate the polymeric calcified valve's feasibility for studies related to transcatheter heart valves. Through multiple experiments, it was found that the polymeric calcified valves can suitably mimic the function of a native calcified stenotic aortic valve and can be used for valve-in-valve studies. Thus, using this unique polymeric calcified valve may be a desired cost-saving solution for testing the performance of new TAVR systems in vitro.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may, in various embodiments, occur in any desired order and fall within the scope of the present invention.

What is claimed is:

1. A calcific polymeric valve, comprising:
a valve structure with at least two leaflets made of a polymeric material, with at least one of the at least two leaflets having a layer formed of a mixture consisting of calcium phosphate and polyurethane, resulting in calcium apatite inclusions formed on the at least one leaflet to replicate naturally-calcified nodules and deposits.

2. The valve as set forth in claim 1, wherein the calcium apatite is randomly distributed within the valve structure.

3. The valve as set forth in claim 1, wherein the valve is implantable via transcatheter means.

4. The valve as set forth in claim 1, wherein the valve is implantable surgically.

5. The valve as set forth in claim 1, wherein the valve is a heart valve.

6. The valve as set forth in claim 1, wherein the valve is a venous valve.

7. The valve as set forth in claim 1, wherein the polymeric material is a silicone polymer or polyurethane.

8. The valve as set forth in claim 1, wherein the valve is made according to radiologic images of patients as obtained from magnetic resonance imagining (MRI) or a computerized tomography (CT) scan.

9. The valve as set forth in claim 1, wherein the valve is formed by a three-dimensional (3D) printer.

10. A calcific polymeric valve, comprising:
a valve structure having at least one leaflet made of a polymeric material with a molded layer formed of a mixture of calcium phosphate and polyurethane, resulting in calcium apatite inclusions randomly formed on the at least one leaflet to replicate naturally-formed calcified nodules and deposits.

* * * * *